US009549863B2

(12) United States Patent
Jackson et al.

(10) Patent No.: US 9,549,863 B2
(45) Date of Patent: Jan. 24, 2017

(54) SURGICAL TABLE WITH PIVOTING AND TRANSLATING HINGE

(71) Applicant: Roger P. Jackson, Prairie Village, KS (US)

(72) Inventors: Roger P. Jackson, Prairie Village, KS (US); Lawrence E. Guerra, Mission, KS (US); Trevor A. Waggoner, Kansas City, KS (US)

(73) Assignee: Roger P. Jackson, Prairie Village, KS (US)

( * ) Notice: Subject to any disclaimer, the term of this patent is extended or adjusted under 35 U.S.C. 154(b) by 0 days.

(21) Appl. No.: 14/792,216

(22) Filed: Jul. 6, 2015

(65) Prior Publication Data

US 2016/0000621 A1    Jan. 7, 2016

Related U.S. Application Data

(60) Provisional application No. 62/021,481, filed on Jul. 7, 2014, provisional application No. 62/118,282, filed
(Continued)

(51) Int. Cl.
*A47G 7/00* (2006.01)
*A61G 7/015* (2006.01)
(Continued)

(52) U.S. Cl.
CPC ............ *A61G 7/015* (2013.01); *A61B 6/0407* (2013.01); *A61G 13/02* (2013.01); *A61G 13/04* (2013.01);
(Continued)

(58) Field of Classification Search
CPC .. A61G 7/015; A61G 13/0018; A61G 13/036; A61G 13/04; A61G 13/08
See application file for complete search history.

(56) References Cited

U.S. PATENT DOCUMENTS 377,377 A  *  2/1888  Ferry ..................... A61G 7/015
                                                                5/617
392,743 A     11/1888  Millen
(Continued)

FOREIGN PATENT DOCUMENTS

CN    2467091 Y    12/2001
EP    2226010 B1    6/2014
(Continued)

OTHER PUBLICATIONS

Brochure of Smith & Nephew on Spinal Positioning System, 2003, 2004.
(Continued)

*Primary Examiner* — Robert G Santos
*Assistant Examiner* — Myles Throop
(74) *Attorney, Agent, or Firm* — Polsinelli PC

(57) ABSTRACT

A surgical table including a patient support structure and a base assembly including a first and a second support column supporting respective ends of the patient support structure. The patient support structure including a head end section and a foot end section, the head end section coupled at a pair of outer ends to the first support column, the foot end section coupled at a pair of outer ends to the second support column, the head and foot end sections each comprising a pair of inner ends that are pivotally and slidingly coupled together at an inward articulation, each of the inner ends of the head end section comprise a slot at the inward articulation, each of the inner ends of the foot end section are coupled with the respective slot via a hinge pin that engages the slot, the hinge pin configured to pivot and slide within the slot.

42 Claims, 33 Drawing Sheets

Related U.S. Application Data on Feb. 19, 2015, provisional application No. 62/118,305, filed on Feb. 19, 2015, provisional application No. 62/021,630, filed on Jul. 7, 2014, provisional application No. 62/021,643, filed on Jul. 7, 2014, provisional application No. 62/021,595, filed on Jul. 7, 2014.

(51) Int. Cl.

| | | |
|---|---|---|
| *A61G 13/02* | (2006.01) | |
| *A61G 13/04* | (2006.01) | |
| *A61B 6/04* | (2006.01) | |
| *A61G 13/08* | (2006.01) | |
| *A61G 13/10* | (2006.01) | |
| *E05D 9/00* | (2006.01) | |
| *E05D 11/00* | (2006.01) | |
| *A61G 13/06* | (2006.01) | |
| *A61G 13/12* | (2006.01) | |

(52) U.S. Cl.
CPC ............... *A61G 13/06* (2013.01); *A61G 13/08* (2013.01); *A61G 13/10* (2013.01); *A61G 13/104* (2013.01); *A61G 13/122* (2013.01); *A61G 13/123* (2013.01); *E05D 9/00* (2013.01); *E05D 11/0054* (2013.01); *A61G 2200/327* (2013.01); *E05D 2011/0072* (2013.01)

(56) References Cited

U.S. PATENT DOCUMENTS

| | | | |
|---|---|---|---|
| 430,635 A | | 6/1890 | Fox |
| 769,415 A | | 9/1904 | Smock |
| 987,423 A | | 3/1911 | Barnett |
| 1,032,743 A | | 7/1912 | Courtney |
| 1,046,430 A | | 12/1912 | Beitz |
| 1,098,209 A | | 5/1914 | Allen |
| 1,098,477 A | | 6/1914 | Cashman |
| 1,143,618 A | | 6/1915 | Ewald |
| 1,160,451 A | | 11/1915 | Sanford |
| 1,171,713 A | * | 2/1916 | Gilkerson ............ A61G 13/009 5/613 |
| 1,356,467 A | | 10/1920 | Payne |
| 1,404,482 A | | 1/1922 | Sawyer |
| 1,482,439 A | | 2/1924 | McCullough |
| 1,528,835 A | | 3/1925 | McCullough |
| 1,667,982 A | | 5/1928 | Pearson |
| 1,780,399 A | | 11/1930 | Munson |
| 1,799,692 A | | 4/1931 | Knott |
| 1,938,006 A | | 12/1933 | Blanchard |
| 1,990,357 A | | 2/1935 | Ward |
| 2,188,592 A | | 1/1940 | Hosken et al. |
| 2,261,297 A | | 11/1941 | Frederick |
| 2,475,003 A | | 7/1949 | Black |
| 2,636,793 A | | 4/1953 | Meyer |
| 2,688,410 A | | 9/1954 | Nelson |
| 2,792,945 A | | 5/1957 | Brenny |
| 3,046,071 A | | 7/1962 | Shampaine et al. |
| 3,049,726 A | | 8/1962 | Getz |
| 3,281,141 A | | 10/1966 | Smiley et al. |
| 3,302,218 A | | 2/1967 | Stryker |
| 3,584,321 A | * | 6/1971 | Buchanan ............ A61G 13/02 5/601 |
| 3,599,964 A | | 8/1971 | Magni |
| 3,640,416 A | | 2/1972 | Temple |
| 3,766,384 A | | 10/1973 | Anderson |
| 3,814,414 A | | 6/1974 | Chapa |
| 3,827,089 A | | 8/1974 | Grow |
| 3,832,742 A | | 9/1974 | Stryker |
| 3,868,103 A | | 2/1975 | Pageot et al. |
| 3,937,054 A | | 2/1976 | Hortvet et al. |
| 3,988,790 A | | 11/1976 | Mracek et al. |
| 4,101,120 A | | 7/1978 | Seshima |
| 4,131,802 A | | 12/1978 | Braden et al. |
| 4,144,880 A | * | 3/1979 | Daniels ................ A61H 1/0292 606/242 |
| 4,148,472 A | | 4/1979 | Rais et al. |
| 4,175,550 A | | 11/1979 | Leininger et al. |
| 4,186,917 A | | 2/1980 | Rais et al. |
| 4,195,829 A | | 4/1980 | Reser |
| 4,227,269 A | | 10/1980 | Johnston |
| 4,230,100 A | | 10/1980 | Moon |
| 4,244,358 A | | 1/1981 | Pyers |
| 4,292,962 A | | 10/1981 | Krause |
| 4,391,438 A | | 7/1983 | Heffington, Jr. |
| 4,435,861 A | | 3/1984 | Lindley |
| 4,474,364 A | * | 10/1984 | Brendgord ............ A61G 13/08 5/613 |
| 4,503,844 A | | 3/1985 | Siczek |
| 4,552,346 A | | 11/1985 | Schnelle et al. |
| 4,712,781 A | | 12/1987 | Watanabe |
| 4,715,073 A | | 12/1987 | Butler |
| 4,718,077 A | | 1/1988 | Moore et al. |
| 4,763,643 A | | 8/1988 | Vrzalik |
| 4,771,785 A | | 9/1988 | Duer |
| 4,830,337 A | | 5/1989 | Ichiro et al. |
| 4,850,775 A | | 7/1989 | Lee et al. |
| 4,862,529 A | | 9/1989 | Peck |
| 4,872,656 A | | 10/1989 | Brendgord et al. |
| 4,872,657 A | | 10/1989 | Lussi |
| 4,887,325 A | | 12/1989 | Tesch |
| 4,937,901 A | | 7/1990 | Brennan |
| 4,939,801 A | | 7/1990 | Schaal et al. |
| 4,944,500 A | | 7/1990 | Mueller et al. |
| 4,953,245 A | | 9/1990 | Jung |
| 4,970,737 A | | 11/1990 | Sagel |
| 4,989,848 A | | 2/1991 | Monroe |
| 5,013,018 A | | 5/1991 | Sicek et al. |
| 5,088,706 A | | 2/1992 | Jackson |
| 5,131,103 A | | 7/1992 | Thomas et al. |
| 5,131,105 A | | 7/1992 | Harrawood et al. |
| 5,131,106 A | | 7/1992 | Jackson |
| 5,161,267 A | | 11/1992 | Smith |
| 5,163,890 A | | 11/1992 | Perry, Jr. |
| 5,181,289 A | | 1/1993 | Kassai |
| 5,208,928 A | | 5/1993 | Kuck et al. |
| 5,210,887 A | | 5/1993 | Kershaw |
| 5,210,888 A | | 5/1993 | Canfield |
| 5,230,112 A | | 7/1993 | Harrawood et al. |
| 5,231,741 A | | 8/1993 | Maguire |
| 5,239,716 A | | 8/1993 | Fisk |
| 5,274,862 A | | 1/1994 | Palmer, Jr. |
| 5,294,179 A | | 3/1994 | Rudes et al. |
| 5,333,334 A | | 8/1994 | Kassai |
| 5,393,018 A | | 2/1995 | Roth et al. |
| 5,444,882 A | | 8/1995 | Andrews et al. |
| 5,461,740 A | | 10/1995 | Pearson |
| 5,468,216 A | | 11/1995 | Johnson et al. |
| 5,487,195 A | | 1/1996 | Ray |
| 5,499,408 A | | 3/1996 | Nix |
| 5,524,304 A | | 6/1996 | Shutes |
| 5,544,371 A | | 8/1996 | Fuller |
| 5,579,550 A | | 12/1996 | Bathrick et al. |
| 5,588,705 A | | 12/1996 | Chang |
| 5,613,254 A | | 3/1997 | Clayman et al. |
| 5,640,730 A | | 6/1997 | Godette |
| 5,645,079 A | | 7/1997 | Zahiri et al. |
| 5,658,315 A | | 8/1997 | Lamb et al. |
| 5,659,909 A | | 8/1997 | Pfeuffer et al. |
| 5,673,443 A | | 10/1997 | Marmor |
| 5,737,781 A | | 4/1998 | Votel |
| 5,754,997 A | | 5/1998 | Lussi et al. |
| 5,774,914 A | | 7/1998 | Johnson et al. |
| 5,794,286 A | | 8/1998 | Scott et al. |
| 5,829,077 A | | 11/1998 | Neige |
| 5,862,549 A | | 1/1999 | Morton et al. |
| 5,870,784 A | | 2/1999 | Elliott |
| 5,890,238 A | | 4/1999 | Votel |
| 5,901,388 A | | 5/1999 | Cowan |
| 5,937,456 A | | 8/1999 | Norris |
| 5,940,911 A | | 8/1999 | Wang |
| 5,996,151 A | | 12/1999 | Bartow et al. |

(56) References Cited

U.S. PATENT DOCUMENTS

| | | | |
|---|---|---|---|
| 6,000,076 A | 12/1999 | Webster et al. | |
| 6,035,465 A | 3/2000 | Rogozinski | |
| 6,049,923 A | 4/2000 | Ochiai | |
| 6,058,532 A | 5/2000 | Allen | |
| 6,109,424 A | 8/2000 | Doan | |
| 6,212,713 B1 | 4/2001 | Kuck et al. | |
| 6,224,037 B1 | 5/2001 | Novick | |
| 6,240,582 B1 | 6/2001 | Reinke | |
| 6,260,220 B1 | 7/2001 | Lamb et al. | |
| 6,282,736 B1 | 9/2001 | Hand et al. | |
| 6,282,738 B1 | 9/2001 | Heimbrock et al. | |
| 6,286,164 B1 | 9/2001 | Lamb et al. | |
| 6,287,241 B1 | 9/2001 | Ellis | |
| 6,295,666 B1 | 10/2001 | Takaura | |
| 6,295,671 B1 | 10/2001 | Reesby et al. | |
| 6,315,564 B1 | 11/2001 | Levisman | |
| 6,322,251 B1 | 11/2001 | Ballhaus et al. | |
| 6,438,777 B1 | 8/2002 | Bender | |
| 6,496,991 B1 | 12/2002 | Votel | |
| 6,499,162 B1 | 12/2002 | Lu | |
| 6,505,365 B1 | 1/2003 | Hanson et al. | |
| 6,526,610 B1 | 3/2003 | Hand et al. | |
| 6,634,043 B2 | 10/2003 | Lamb et al. | |
| 6,638,299 B2 | 10/2003 | Cox | |
| 6,662,388 B2 | 12/2003 | Friel | |
| 6,668,396 B2 | 12/2003 | Wei | |
| 6,681,423 B2 | 1/2004 | Zachrisson | |
| 6,701,553 B1 | 3/2004 | Hand et al. | |
| 6,779,210 B1 | 8/2004 | Kelly | |
| 6,791,997 B2 | 9/2004 | Beyer et al. | |
| 6,794,286 B2 | 9/2004 | Aoyama et al. | |
| 6,817,363 B2 | 11/2004 | Biondo et al. | |
| 6,854,137 B2 | 2/2005 | Johnson | |
| 6,857,144 B1 | 2/2005 | Huang | |
| 6,862,759 B2 | 3/2005 | Hand et al. | |
| 6,885,165 B2 | 4/2005 | Henley et al. | |
| 6,971,131 B2 | 12/2005 | Bannister | |
| 6,971,997 B1 | 12/2005 | Ryan et al. | |
| 7,003,828 B2 | 2/2006 | Roussy | |
| 7,055,195 B2 | 6/2006 | Roussy | |
| 7,089,612 B2 | 8/2006 | Rocher et al. | |
| 7,103,931 B2 | 9/2006 | Somasundaram et al. | |
| 7,137,160 B2 | 11/2006 | Hand et al. | |
| 7,152,261 B2 | 12/2006 | Jackson | |
| 7,171,709 B2 | 2/2007 | Weismiller | |
| 7,189,214 B1 | 3/2007 | Saunders | |
| 7,197,778 B2 | 4/2007 | Sharps | |
| 7,213,279 B2 | 5/2007 | Weismiller et al. | |
| 7,234,180 B2 | 6/2007 | Horton et al. | |
| 7,290,302 B2 | 11/2007 | Sharps | |
| 7,331,557 B2 | 2/2008 | Dewert | |
| 7,428,760 B2 | 9/2008 | McCrimmon | |
| 7,437,785 B2 | 10/2008 | Farooqui | |
| 7,552,490 B2 | 6/2009 | Saracen et al. | |
| 7,596,820 B2 | 10/2009 | Nielsen et al. | |
| 7,653,953 B2 | 2/2010 | Lopez-Sansalvador | |
| 7,669,262 B2 | 3/2010 | Skripps et al. | |
| 7,739,762 B2 | 6/2010 | Lamb et al. | |
| 7,874,030 B2 | 1/2011 | Cho et al. | |
| 7,874,695 B2 | 1/2011 | Jensen | |
| 8,056,163 B2 | 11/2011 | Lemire et al. | |
| 8,060,960 B2* | 11/2011 | Jackson | A61G 7/001 5/607 |
| 8,381,331 B2 | 2/2013 | Sharps et al. | |
| 8,584,281 B2* | 11/2013 | Diel | A61G 13/0036 5/601 |
| 8,635,725 B2 | 1/2014 | Tannoury et al. | |
| 8,677,529 B2 | 3/2014 | Jackson | |
| 8,707,476 B2 | 4/2014 | Sharps | |
| 8,719,979 B2 | 5/2014 | Jackson | |
| 8,826,474 B2 | 9/2014 | Jackson | |
| 8,826,475 B2 | 9/2014 | Jackson | |
| 8,839,471 B2 | 9/2014 | Jackson | |
| 8,844,077 B2 | 9/2014 | Jackson et al. | |
| 8,856,986 B2 | 10/2014 | Jackson | |
| D720,076 S | 12/2014 | Sharps et al. | |
| 8,938,826 B2 | 1/2015 | Jackson | |
| 8,978,180 B2 | 3/2015 | Jackson | |
| 9,180,062 B2 | 11/2015 | Jackson | |
| 9,186,291 B2 | 11/2015 | Jackson et al. | |
| 9,198,817 B2 | 12/2015 | Jackson | |
| 9,205,013 B2 | 12/2015 | Jackson | |
| 9,211,223 B2* | 12/2015 | Jackson | A61G 7/001 |
| 9,265,680 B2 | 2/2016 | Sharps et al. | |
| 2001/0037524 A1 | 11/2001 | Truwit | |
| 2002/0170116 A1 | 11/2002 | Borders et al. | |
| 2003/0074735 A1 | 4/2003 | Zachrisson | |
| 2003/0145383 A1* | 8/2003 | Schwaegerle | A61G 13/04 5/610 |
| 2004/0098804 A1 | 5/2004 | Varadharajulu et al. | |
| 2004/0133983 A1 | 7/2004 | Newkirk et al. | |
| 2004/0168253 A1 | 9/2004 | Hand et al. | |
| 2004/0219002 A1 | 11/2004 | Lenaers et al. | |
| 2006/0185091 A1* | 8/2006 | Jackson | A61G 7/001 5/621 |
| 2006/0248650 A1 | 11/2006 | Skripps | |
| 2007/0056105 A1 | 3/2007 | Hyre et al. | |
| 2007/0107126 A1 | 5/2007 | Koch et al. | |
| 2007/0157385 A1 | 7/2007 | Lemire et al. | |
| 2007/0174965 A1 | 8/2007 | Lemire et al. | |
| 2007/0192960 A1* | 8/2007 | Jackson | A61G 7/001 5/618 |
| 2007/0266516 A1 | 11/2007 | Cakmak | |
| 2008/0216241 A1 | 9/2008 | Mangiardi | |
| 2009/0126116 A1 | 5/2009 | Lamb et al. | |
| 2009/0235456 A1 | 9/2009 | Bock | |
| 2010/0037397 A1* | 2/2010 | Wood | A61G 7/015 5/657 |
| 2010/0107790 A1 | 5/2010 | Yamaguchi | |
| 2010/0192300 A1 | 8/2010 | Tannoury et al. | |
| 2010/0223728 A1 | 9/2010 | Hutchison et al. | |
| 2011/0099716 A1* | 5/2011 | Jackson | A61G 13/0036 5/607 |
| 2011/0107517 A1 | 5/2011 | Lamb et al. | |
| 2011/0197361 A1 | 8/2011 | Hornbach et al. | |
| 2012/0005832 A1 | 1/2012 | Turner et al. | |
| 2012/0144589 A1 | 6/2012 | Skripps et al. | |
| 2012/0174319 A1* | 7/2012 | Menkedick | A61G 7/005 5/618 |
| 2012/0198625 A1 | 8/2012 | Jackson | |
| 2012/0246829 A1 | 10/2012 | Lamb et al. | |
| 2012/0246830 A1* | 10/2012 | Hornbach | A61G 7/015 5/619 |
| 2013/0111666 A1 | 5/2013 | Jackson | |
| 2013/0133137 A1* | 5/2013 | Jackson | A61G 13/08 5/617 |
| 2013/0198958 A1 | 8/2013 | Jackson et al. | |
| 2013/0219623 A1 | 8/2013 | Jackson | |
| 2013/0254995 A1 | 10/2013 | Jackson | |
| 2013/0269710 A1 | 10/2013 | Hight et al. | |
| 2013/0282234 A1 | 10/2013 | Roberts et al. | |
| 2013/0312181 A1 | 11/2013 | Jackson et al. | |
| 2013/0312187 A1 | 11/2013 | Jackson | |
| 2013/0312188 A1* | 11/2013 | Jackson | A61G 7/015 5/618 |
| 2014/0007349 A1 | 1/2014 | Jackson | |
| 2014/0020181 A1 | 1/2014 | Jackson | |
| 2014/0033436 A1 | 2/2014 | Jackson | |
| 2014/0068861 A1 | 3/2014 | Jackson et al. | |
| 2014/0082842 A1 | 3/2014 | Jackson | |
| 2014/0109316 A1* | 4/2014 | Jackson | A61G 13/0036 5/601 |
| 2014/0173826 A1 | 6/2014 | Jackson | |
| 2014/0196212 A1 | 7/2014 | Jackson | |
| 2014/0201913 A1 | 7/2014 | Jackson | |
| 2014/0201914 A1 | 7/2014 | Jackson | |
| 2014/0208512 A1 | 7/2014 | Jackson | |
| 2014/0317847 A1 | 10/2014 | Jackson | |
| 2015/0007391 A1* | 1/2015 | Xu | A61G 7/018 5/616 |
| 2015/0059094 A1 | 3/2015 | Jackson | |
| 2015/0113733 A1 | 4/2015 | Diel et al. | |
| 2015/0150743 A1 | 6/2015 | Jackson | |

(56) References Cited

U.S. PATENT DOCUMENTS

| | | | |
|---|---|---|---|
| 2016/0000620 | A1 | 1/2016 | Koch |
| 2016/0000621 | A1* | 1/2016 | Jackson ................ A61G 13/06 5/618 |
| 2016/0000626 | A1* | 1/2016 | Jackson ................ A61G 13/06 5/608 |
| 2016/0000627 | A1* | 1/2016 | Jackson ................ A61G 13/02 5/608 |
| 2016/0000629 | A1 | 1/2016 | Jackson et al. |
| 2016/0008201 | A1 | 1/2016 | Jackson et al. |
| 2016/0038364 | A1 | 2/2016 | Jackson |
| 2016/0136027 | A1 | 5/2016 | Jackson |
| 2016/0166452 | A1 | 6/2016 | Jackson et al. |
| 2016/0213542 | A1 | 7/2016 | Jackson |

FOREIGN PATENT DOCUMENTS

| | | |
|---|---|---|
| GB | 569758 | 6/1945 |
| GB | 910956 | 3/1959 |
| JP | S53763 | 1/1978 |
| JP | 2000-060995 | 2/2000 |
| JP | 2000-116733 | 4/2000 |
| WO | WO99/07320 | 2/1999 |
| WO | WO 00/07537 | 2/2000 |
| WO | WO00/062731 | 10/2000 |
| WO | WO01/060308 | 8/2001 |
| WO | WO03/070145 | 8/2003 |
| WO | WO2007/130679 A2 | 11/2007 |
| WO | WO2009/054969 | 4/2009 |
| WO | WO2009/100692 | 8/2009 |
| WO | WO2010/051303 A1 | 5/2010 |

OTHER PUBLICATIONS

Complaint for Patent Infringement, *Jackson v. Mizuho Orthopedic Sys., Inc.*, No. 4:12-CV-01031 (W.D. Mo. Aug. 7, 2012).
First Amended Complaint for Patent Infringement and Correction of Inventorship, *Jackson v. Mizuho Orthopedic Sys., Inc.*, No. 4:12-CV-01031 (W.D. Mo. Sep. 21, 2012).
Defendant Mizuho Orthopedic Systems, Inc.'s Answer To First Amended Complaint And Counterclaims, *Jackson v. Mizuho Orthopedic Sys., Inc.*, No. 4:12-CV-01031 (W.D. Mo. Nov. 1, 2012).
Plaintiff Roger P. Jackson, MD's, Reply To Counterclaims, *Jackson v. Mizuho Orthopedic Sys., Inc.*, No. 4:12-CV-01031 (W.D. Mo. Nov. 26, 2012).
Roger P. Jackson's Disclosure Of Asserted Claims And Preliminary Infringement Contentions, *Jackson v. Mizuho Orthopedic Sys., Inc.*, No. 4:12-CV-01031 (W.D. Mo. Jan. 4, 2013).
Second Amended Complaint for Patent Infringement, For Correction Of Inventorship, For Breach Of A Non-Disclosure And Confidentiality Agreement, And For Misappropriation Of Dr. Jackson's Right Of Publicity, *Jackson v. Mizuho Orthopedic Sys., Inc.*, No. 4:12-CV-01031 (W.D. Mo. Jan. 28, 2013).
Defendant Mizuho Orthopedic Systems, Inc.'s Answer To Second Amended Complaint And Counterclaims, *Jackson v. Mizuho Orthopedic Sys., Inc.*, No. 4:12-CV-01031 (W.D. Mo. Feb. 19, 2013).
Defendant Mizuho Osi's Invalidity Contentions Pursuant To The Parties' Joint Scheduling Order, *Jackson v. Mizuho Orthopedic Sys., Inc.*, No. 4:12-CV-01031 (W.D. Mo. Feb. 22, 2013).
Plaintiff Roger P. Jackson, MD's, Reply To Second Counterclaims, *Jackson v. Mizuho Orthopedic Sys., Inc.*, No. 4:12-CV-01031 (W.D. Mo. Mar. 12, 2013).
Roger P. Jackson, MD's Disclosure Of Proposed Terms To Be Construed, *Jackson v. Mizuho Orthopedic Sys., Inc.*, No. 4:12-CV-01031 (W.D. Mo. Apr. 5, 2013).
Defendant Mizuho Orthopedic Systems, Inc.'s Disclosure of Proposed Terms and Claim Elements for Construction, *Jackson v. Mizuho Orthopedic Sys., Inc.*, No. 4:12-CV-01031 (W.D. Mo. Apr. 5, 2013).
Mizuho Orthopedic Systems, Inc.'s Disclosure Of Proposed Claim Constructions And Extrinsic Evidence, *Jackson v. Mizuho Orthopedic Sys., Inc.*, No. 4:12-CV-01031 (W.D. Mo. May 13, 2013).
Plaintiff Roger P. Jackson, MD's Disclosure Of Preliminary Proposed Claim Constructions, *Jackson v. Mizuho Orthopedic Sys., Inc.*, No. 4:12-CV-01031 (W.D. Mo. May 13, 2013).
Defendant Mizuho Osi's Amended Invalidity Contentions Pursuant To The Parties' Joint Scheduling Order, *Jackson v. Mizuho Orthopedic Sys., Inc.*, No. 4:12-CV-01031 (W.D. Mo. May 15, 2013).
Joint Claim Construction Chart and Joint Prehearing Statement, *Jackson v. Mizuho Orthopedic Sys., Inc.*, No. 4:12-CV-01031 (W.D. Mo. Jun. 7, 2013).
Defendant Mizuho Orthopedic Systems, Inc.'s Objections And Responses To Plaintiff's First Set Of Interrogatories, *Jackson v. Mizuho Orthopedic Sys., Inc.*, No. 4:12-CV-01031 (W.D. Mo. Jun. 24, 2013).
Defendant Mizuho Orthopedic Systems, Inc.'s Opening Claim Construction Brief, *Jackson v. Mizuho Orthopedic Sys., Inc.*, No. 4:12-CV-01031 (W.D. Mo. Jul. 31, 2013).
Plaintiff Roger P. Jackson, MD's Opening Claim Construction Brief, *Jackson v. Mizuho Orthopedic Sys., Inc.*, No. 4:12-CV-01031 (W.D. Mo. Jul. 31, 2013).
Appendix A Amended Infringement Contentions Claim Chart For Mizuho's Axis System Compared To U.S. Pat. No. 7,565,708, *Jackson v. Mizuho Orthopedic Sys., Inc.*, No. 4:12-CV-01031 (W.D. Mo. Aug. 12, 2013).
Appendix B Amended Infringement Contentions Claim Chart For Mizuho's Axis System Compared To U.S. Pat. No. 8,060,960, *Jackson v. Mizuho Orthopedic Sys., Inc.*, No. 4:12-CV-01031 (W.D. Mo. Aug. 12, 2013).
Appendix C Amended Infringement Contentions Claim Chart For Mizuho's Proaxis System Compared To U.S. Pat. No. 7,565,708, *Jackson v. Mizuho Orthopedic Sys., Inc.*, No. 4:12-CV-01031 (W.D. Mo. Aug. 12, 2013).
Appendix D Amended Infringement Contentions Claim Chart For Mizuho's Proaxis System Compared To U.S. Pat. No. 8,060,960, *Jackson v. Mizuho Orthopedic Sys., Inc.*, No. 4:12-CV-01031 (W.D. Mo. Aug. 12, 2013).
Plaintiff Roger P. Jackson, MD's Responsive Claim Construction Brief, *Jackson v. Mizuho Orthopedic Sys., Inc.*, No. 4:12-CV-01031 (W.D. Mo. Aug. 16, 2013).
Defendant Mizuho Orthopedic Systems, Inc's Brief In Response to Plaintiff's Opening Claim Construction Brief, *Jackson v. Mizuho Orthopedic Sys., Inc.*, No. 4:12-CV-01031 (W.D. Mo. Aug. 16, 2013).
Plaintiff Roger P. Jackson, Md's Suggestions In Support Of His Motion To Strike Exhibit A Of Mizuho's Opening Claim Construction Brief, *Jackson v. Mizuho Orthopedic Sys., Inc.*, No. 4:12-CV-01031 (W.D. Mo. Aug. 16, 2013).
Defendant Mizuho Orthopedic Systems, Inc.'s Opposition To Plaintiff's Motion To Strike, *Jackson v. Mizuho Orthopedic Sys., Inc.*, No. 4:12-CV-01031 (W.D. Mo. Sep. 3, 2013).
Transcript of Claim Construction Hearing, *Jackson v. Mizuho Orthopedic Sys., Inc.*, No. 4:12-CV-01031 (W.D. Mo. Oct. 11, 2013).
Plaintiff Roger P. Jackson, MD's Claim Construction Presentation for U.S. District Judge Nanette K. Laughrey, *Jackson v. Mizuho Orthopedic Sys., Inc.*, No. 4:12-CV-01031 (W.D. Mo. Oct. 11, 2013).
Mizuho's Claim Construction Argument, *Jackson v. Mizuho Orthopedic Sys., Inc.*, No. 4:12-CV-01031 (W.D. Mo. Oct. 11, 2013).
Order, *Jacksonv. Mizuho Orthopedic Sys., Inc.*, No. 4:12-CV-01031 (W.D. Mo. Apr. 4, 2014).
Brochure of OSI on Modular Table System 90D, pp. 1-15, date of first publication: Unknown.
Pages from website http://www.schaerermayfieldusa.com, ppp 1-5, date of first publication: Unknown.
European Search Report, EP11798501.0, dated Mar. 30, 2015.
Canadian Office Action, CA2803110, dated Mar. 5, 2015.
Chinese Office Action, CN 201180039162.0, dated Jan. 19, 2015.
Japanese Office Action, JP 2014-142074, dated Jun. 18, 2015.
Japanese Office Action, JP 2014-132463, dated Jun. 18, 2015.
Quayle Action, U.S. Appl. No. 14/792,216, dated Sep. 9, 2015.
Australian Patent Examination Report No. 2, AU2014200274, dated Oct. 9, 2015.

(56) References Cited

OTHER PUBLICATIONS

European Examination Report, EP11798501.0, dated Nov. 12, 2015.
Japanese Final Rejection (English version), JP 2014-142074, dated Dec. 6, 2015.
International Search Report and Written Opinion of the International Searching Authority, PCT/US2015/039400, dated Dec. 7, 2015, 13 pages.
U.S. Appl. No. 15/207,599, filed Jul. 12, 2016, Jackson.
Japanese Office Action, JP 2016-041088, dated Apr. 12, 2016.

* cited by examiner

SURGICAL TABLE WITH PIVOTING AND TRANSLATING HINGE

CROSS-REFERENCE TO RELATED APPLICATIONS

The present application claims priority under 35 U.S.C. §119 to U.S. Provisional Patent Application No. 62/021,481, filed on Jul. 7, 2014, titled "RADIOLUCENT HINGE FOR A SURGICAL TABLE", which is hereby incorporated by reference in its entirety into the present application.

The present application claims priority under 35 U.S.C. §119 to U.S. Provisional Patent Application No. 62/118,282, filed on Feb. 19, 2015, titled "RADIOLUCENT HINGE FOR A SURGICAL TABLE", which is hereby incorporated by reference in its entirety into the present application.

The present application claims priority under 35 U.S.C. §119 to U.S. Provisional Patent Application No. 62/118,305, filed on Feb. 19, 2015, titled "SINGLE COLUMN PATIENT POSITIONING AND SUPPORT STRUCTURE", which is hereby incorporated by reference in its entirety into the present application.

The present application claims priority under 35 U.S.C. §119 to U.S. Provisional Patent Application No. 62/021,630, filed on Jul. 7, 2014, titled "SURGICAL TABLE WITH PATIENT SUPPORT HAVING FLEXIBLE INNER FRAME SUPPORTED ON RIGID OUTER FRAME", which is hereby incorporated by reference in its entirety into the present application.

The present application claims priority under 35 U.S.C. §119 to U.S. Provisional Patent Application No. 62/021,643, filed on Jul. 7, 2014, titled "SINGLE COLUMN PATIENT POSITIONING SUPPORT STRUCTURE", which is hereby incorporated by reference in its entirety into the present application.

The present application claims priority under 35 U.S.C. §119 to U.S. Provisional Patent Application No. 62/021,595, filed on Jul. 7, 2014, titled "PATIENT SUPPORT STRUCTURE WITH PIVOTING AND TRANSLATING HINGE", which is hereby incorporated by reference in its entirety into the present application.

TECHNICAL FIELD

Aspects of the present disclosure involve a surgical table and, more particularly, involve a surgical table with a pivoting and longitudinally translating hinge.

BACKGROUND

From scalpels to surgical tables, surgeons rely on a multitude of specially designed tools and apparatuses to perform surgical procedures. In any number of procedures, a surgeon may need to position a patient in various positions (e.g., roll, Trendelenburg, reverse Trendelenburg, raise and lower, flex and extend) throughout the surgery in order to perform various steps of the procedure. Positioning the patient in the various positions may require the use of a specialized table or support structure that is uniquely designed to facilitate the required movements for the procedure. With certain support structures, articulating different portions of the support structure poses problems. In particular, support structures with certain types of articulating hinges fixed between head and foot end sections of a suspended patient support structure tend to require the use of a "trunk translator" or other device that allows the patient's torso to slide on the head end section of the patient support structure when the structure pivots about the hinges. In doing so, significant translation of the patient's head and torso are required with respect to anesthesia. In addition to adding an assembly to the support structure, such devices are often not radiolucent, which also poses problems for generating medical images. And, since certain procedures (e.g., spinal surgery) may require the patient to undergo medical imaging during the procedure, it is desirable for the patient support structure to be made from radiolucent materials (e.g., carbon fiber, PEEK, polymer, among other materials). In addition to the various positioning and materials requirements on surgical support structures, laws and regulations may provide additional requirements for safely positioning patients during a surgical procedure that must be considered.

With these thoughts in mind, among others, aspects of the surgical table with a pivoting and translating hinge disclosed herein were conceived.

SUMMARY

Aspects of the present disclosure involve a surgical table including a patient support structure and a base assembly. The base assembly includes a first and a second support column supporting respective ends of the patient support structure. The patient support structure includes a head end section and a foot end section, the head end section coupled at a pair of outer ends to the first support column. The foot end section may be coupled at a pair of outer ends to the second support column. The head and foot end sections may each include a pair of inner ends that are pivotally and slidingly coupled together at an inward articulation. Each of the inner ends of the head end section may include a slot at the inward articulation. Each of the inner ends of the foot end section may be coupled with the respective slot at the inward articulation via a hinge pin that engages the slot. The hinge pin may be configured to pivot and slide within the slot. The hinge pin may be positionally located in between a head end portion and a foot end portion of the slot when the head and foot end sections are in a neutral position, and the hinge pin may be configured to move towards a foot end portion of the slot when the patient support structure moves from the neutral position to an extended position. It is foreseen that in certain implementations the location of the pins and slots could be reversed with respect to the head and foot end sections.

Aspects of the present disclosure involve a surgical table including a base assembly and a patient support assembly. The base assembly may include a pair of spaced apart end support columns. The patient support structure may include a head end section and a foot end section. The head end section may include a pair of head end members coupled on outer ends with one of the pair of end support columns. The foot end section may include a pair of foot end members coupled on outer ends with another of the pair of end support columns. Each of the head end members may include an inner end with a slot formed therein. Each of the foot end members may be coupled with a respective inner end of the head end member at the slot by a hinge pin configured to pivot and translate within the slot when the head and foot end sections articulate relative to each other. A distance between the hinge pin and the outer ends of the head end members may be configured to increase or decrease when the head end section and the foot end section articulate relative to each other about the hinge pin. The base assembly includes translating and actively driven angulating, articulating, and/or pivoting actuators to support and move the head and foot end sections of the patient support structure with respect to each other and the base assembly end support columns.

BRIEF DESCRIPTION OF THE DRAWINGS

Example embodiments are illustrated in referenced figures of the drawings. It is intended that the embodiments and figures disclosed herein are to be considered illustrative rather than limiting.

DETAILED DESCRIPTION

Aspects of the present disclosure involve a surgical table with a dual-sided, opened-frame patient support structure that articulates between the respective inner ends of the structure. The patient support structure articulates about a pivoting and longitudinally translating sliding hinge such that the patient support structure or a portion thereof matches the movement of a patient's body that is supported on the support structure and, thus, eliminates a need for a "trunk translator" attachment to the patient support structure. More particularly, the patient's torso maintains constant or substantially constant position relative to a torso assembly that is positioned along and coupled to a head end portion or section of the patient support structure, and the patient's pelvis and hips maintain constant or substantially constant position relative to a pair of hip pads coupled to a foot end portion or section of the patient support structure when the patient support structure pivots and translates at the hinge. Without such pivoting and longitudinal translation and adjustment of such a sliding hinge and because the articulations within the patient's body are offset from a hinge axis of a patient support structure, the patient's body would not otherwise maintain constant positioning relative to the pads on the patient support structure (i.e., unless the pads themselves moved along the patient support structure) and unwanted distraction and compression of the patient's body would occur. Certain devices (e.g., trunk translator) are used to longitudinally move the chest pads along the patient support structure, but these devices are usually mechanical linkages or active drive mechanisms that include non-radiolucent materials. Additionally, such devices add assemblies, expense, and weight to the patient support structure, wherein it has been found to be effective to slide the hinge to match the patient's movement, thus, eliminating the need for another device to be added to the surgical table.

Regarding the materials, the patient support structure, including the hinge, may be made from radiolucent materials such that the surgical table may function as a medical imaging table, thus, obviating the need for the patient to switch from a surgical table to an imaging table in order to obtain medical images of the patient before, during, or after a particular surgical procedure.

To begin, the discussion will focus on the surgical table as a whole. Then, the discussion will focus on the individual assemblies of the support structure and, finally, the focus will be on the operation of the surgical table.

Figure 1:
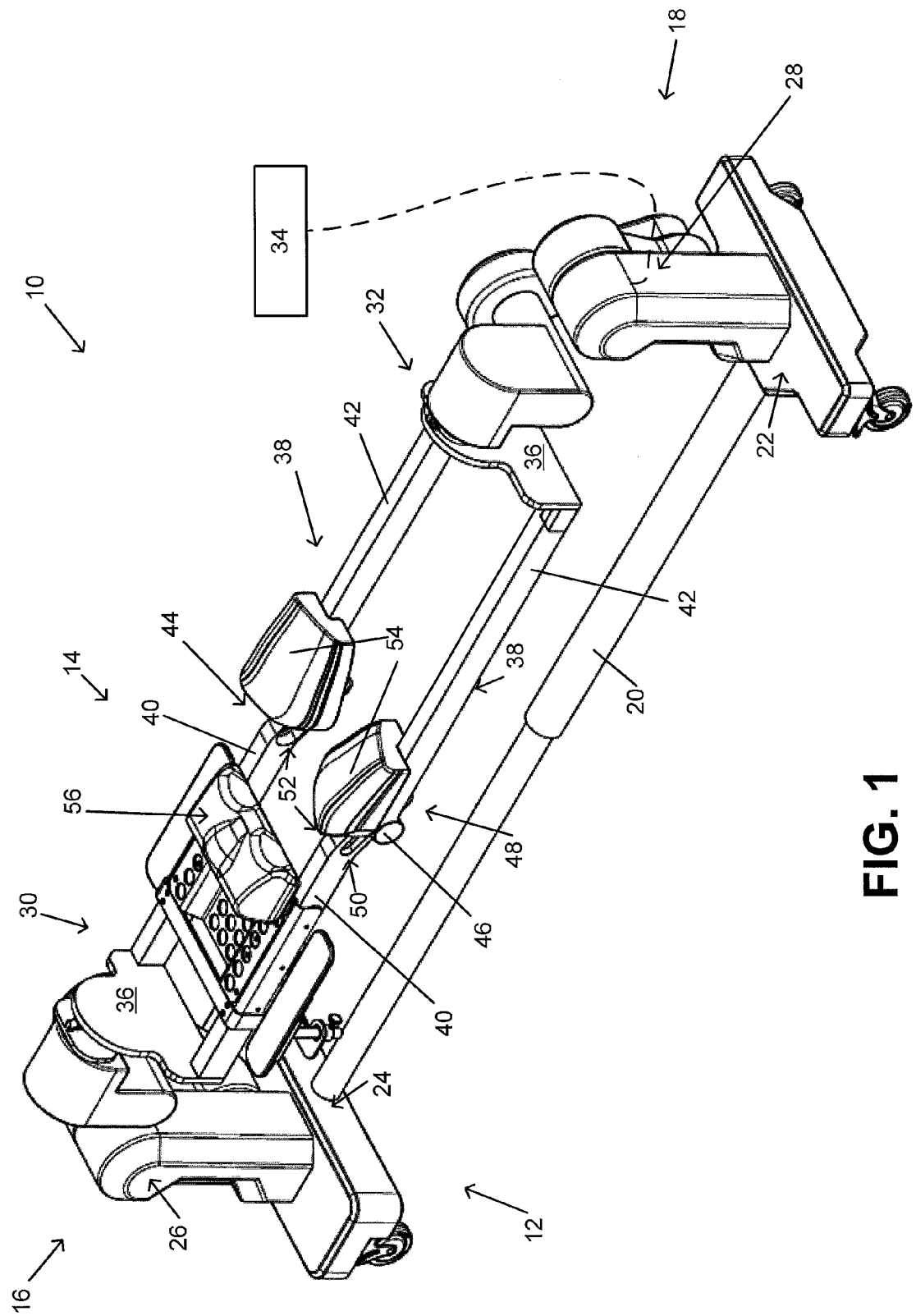
FIG. 1 depicts a top isometric view of a surgical table with a patient support structure having dual translating and pivoting hinges in a neutral position.
Figure 2:
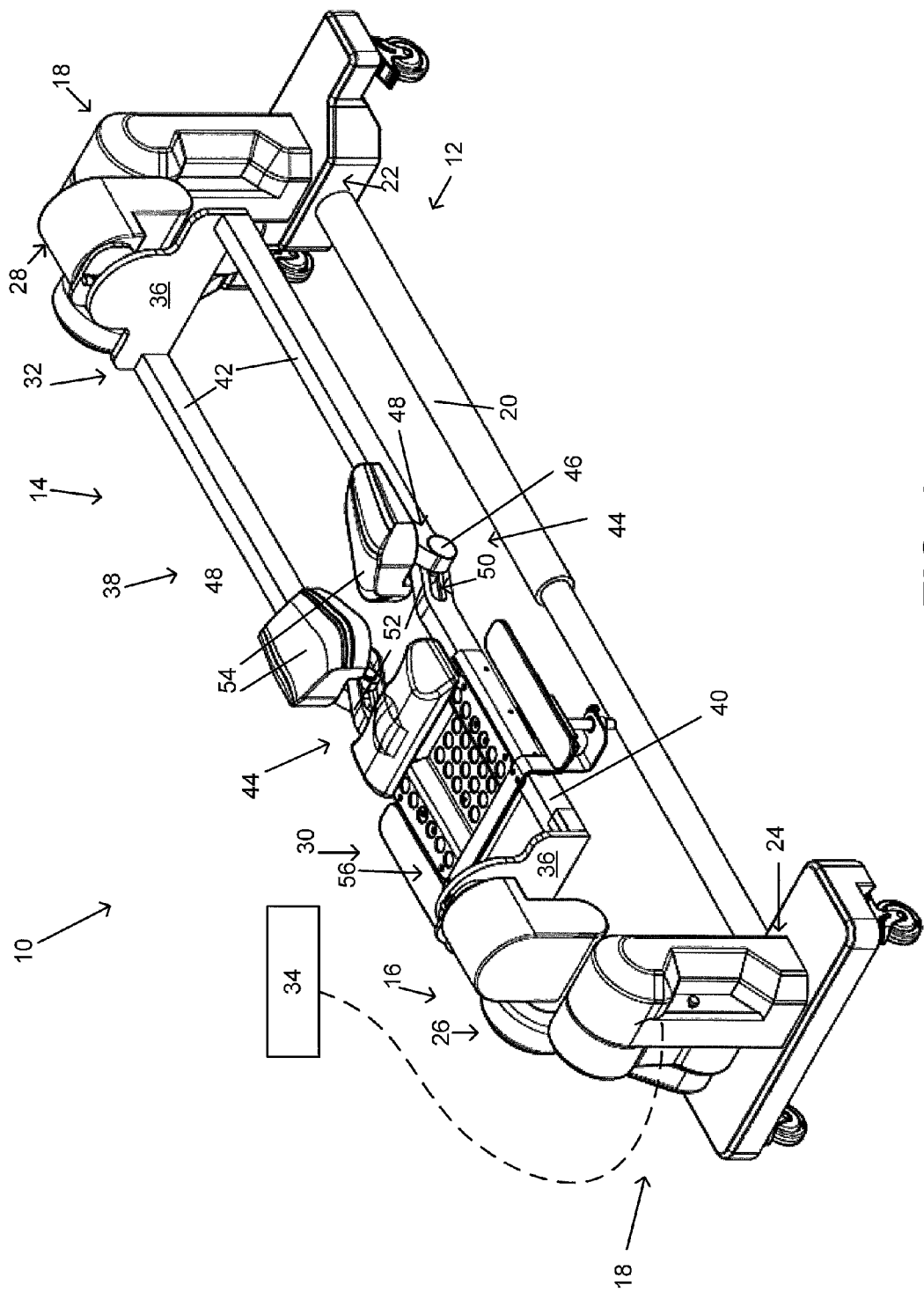
FIG. 2 depicts another top isometric view of the surgical table of FIG. 1.

Reference is now made to FIGS. 1-2, which are top isometric views of a surgical table 10 having a base assembly 12 and a patient support structure 14. As seen in the figures, the base assembly 12 includes a head end support column 16, a foot end support column 18, and a spanning member 20 extending from a bottom portion 22 of the foot end support column 18 to a bottom portion 24 of the head end support column 16. The base assembly 12 additionally includes a head end articulation assembly 26 and a foot end articulation assembly 28. The head end articulation assembly 28 extends from the head end support column 16 and couples with a head end section 30 of the patient support structure 14. The foot end articulation assembly 28 extends from the foot end support column 18 and couples with a foot end section 32 of the patient support structure 14. Each of the articulation assemblies 26, 28 is configured to provide the following movement to its respective end 30, 32 of the patient support structure 14: vertical lift, translation along a longitudinal axis of the support structure (i.e., in a direction of extension of the spanning member 20), axial rotation or roll around the longitudinal axis, transverse translation in a direction perpendicular to the longitudinal axis, and yaw rotation or roll around a yaw axis extending generally parallel with an axis extending vertically through the support columns 16, 18. These various functions may be carried out by any number of motors and, perhaps, linear guides rotationally coupled with lead screws or other mechanisms to provide linear motion. In certain embodiments, all of these functions are actively controlled by a user (e.g., surgeon) operating a user device 34 (e.g., control device in communication with a computer) to control the specific or general functions of the articulation assemblies 26, 28. In other embodiments, certain functions may be passively controlled. For example, in certain implantations and to implement certain commands, the head end articulation assembly 26 may provide vertical lift to the head end section 30 of the patient support structure 14 while passively raising and translating the foot end section 32 of the patient support structure 14 and the foot end articulation assembly 28. In other implementations and to implement certain commands, all functionality, for example, may require powered movement and control from each articulation assembly 26, 28. The specifics of the power and control may vary based on the specific implementation and the specific command signaled by a user with the user device 34.

Accordingly, all such active and passive controls regarding the base assembly 12 and the articulation assemblies 26, 28 are contemplated herein and part of the present disclosure. Additionally, while the base assembly 12 is described herein as including a pair of actuation assemblies 26, 28 in a particular arrangement, other arrangements are possible and contemplated herein. It is intended that the patient support structure 14 described herein is useable with various configurations and arrangements of base assemblies. For example, the base assembly may include other base assemblies or column support assemblies including but not limited to those described in: U.S. Provisional Patent Application No. 62/021,481, filed on Jul. 7, 2014 and titled "RADIOLUCENT HINGE FOR A SURGICAL TABLE"; U.S. Provisional Patent Application No. 62/021,630, filed on Jul. 7, 2014 and titled "SURGICAL TABLE WITH PATIENT SUPPORT HAVING FLEXIBLE INNER FRAME SUPPORTED ON RIGID OUTER FRAME"; U.S. Pat. No. 7,565,708, filed on Apr. 20, 2007 and titled "PATIENT POSITIONING SUPPORT STRUCTURE"; and U.S. patent application Ser. No. 12/803,192, filed on Jun. 21, 2010 and titled "PATIENT POSITIONING SUPPORT STRUCTURE WITH TRUNK TRANSLATOR". All of these applications are hereby incorporated by reference in their entireties into the present application. Assemblies described in the incorporated applications may be used in conjunction with the patient support structure 14 described herein with minor or no additional modifications.

Reference is now made to the patient support structure 14 and still to FIGS. 1-2. The head end section 30 and foot end section 32 of the patient support structure 14 are each coupled with its respective articulation assembly 26, 28 via a mounting plate 36. In particular, the mounting plate 36 couples with respective ends 30, 32 of a pair of articulating support assemblies 38 that collectively form an open-frame support for a patient undergoing a medical procedure. Each of the articulating support assemblies 38 includes a head end member 40 and a foot end member 42 that are pivotally and slidably coupled at a joint 44 by a hinge pin 46. A pair of head end members 40 may be referred to as the head end section and a pair of the foot end members 42 may be referred to as the foot end section. The head and foot end sections may join together at inner ends to a hinge and may be coupled at outer ends to the mounting plate 36.

Figure 3:
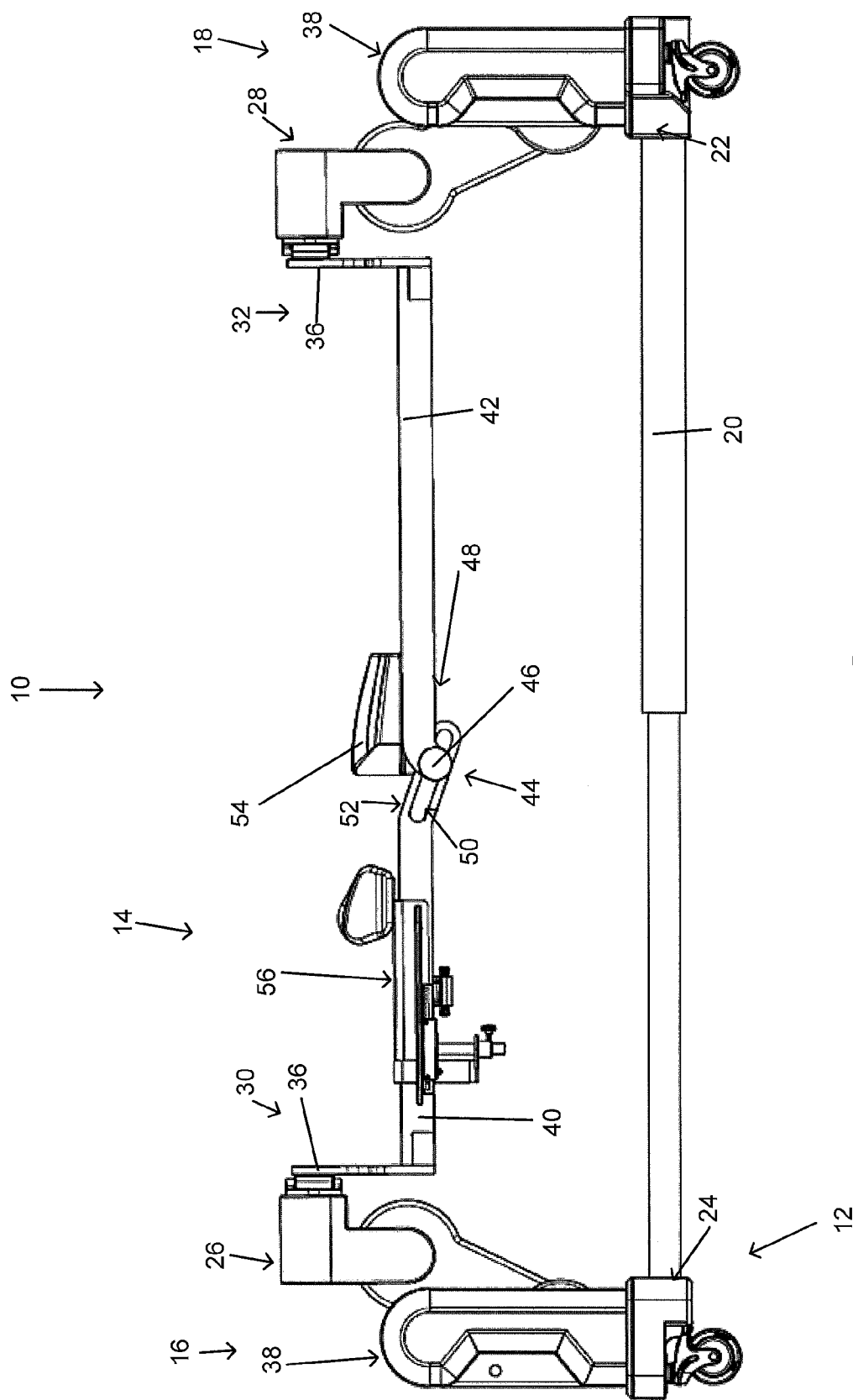
FIG. 3 depicts a first side view of the surgical table of FIG. 1.
Figure 4:
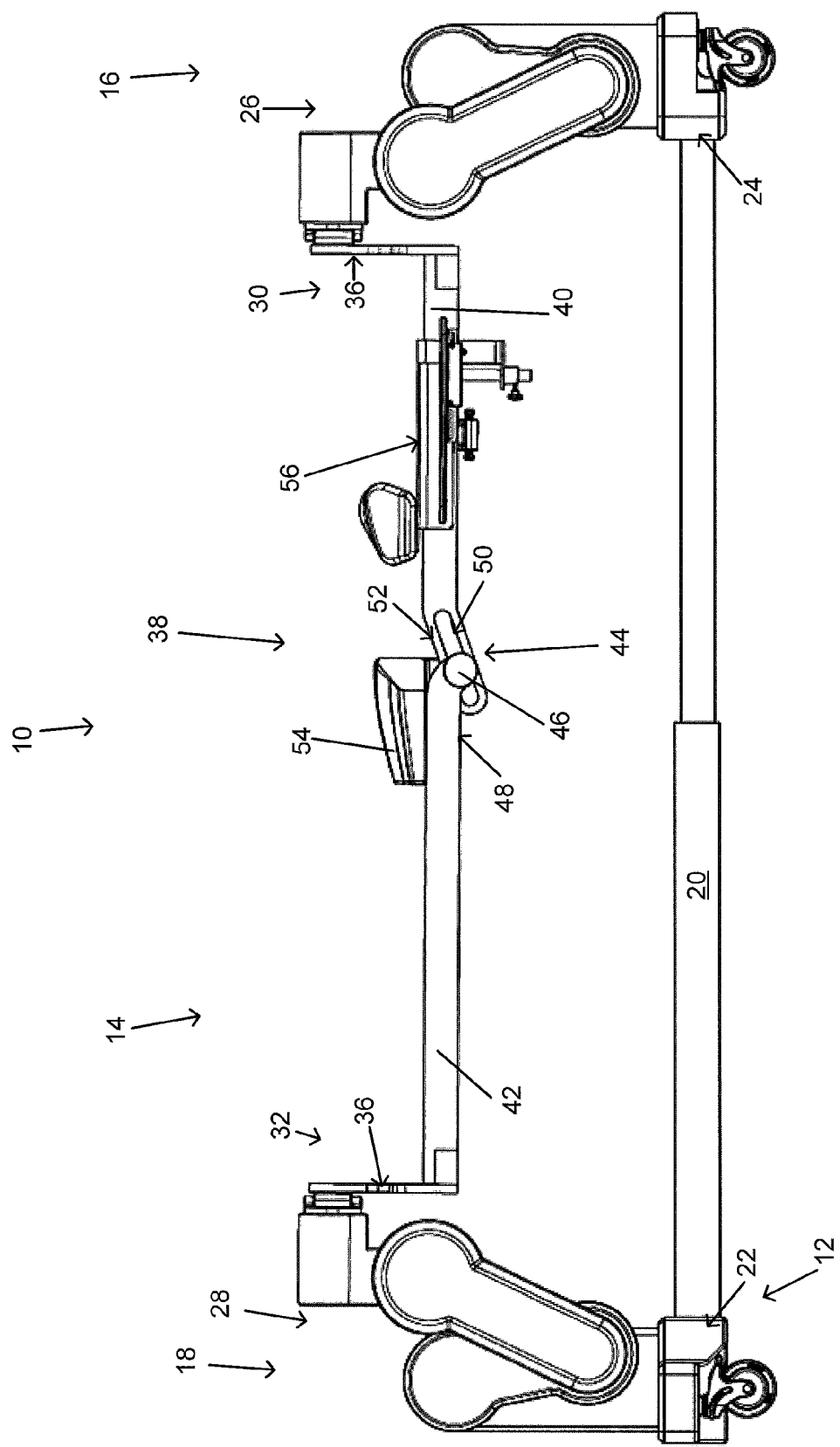
FIG. 4 depicts a second side view of the surgical table of FIG. 1.

As seen in FIGS. 3-4, which are opposite side views of the surgical table 10, the hinge pin 46 is fixedly coupled with a hinge end 48 of the foot end member 42. As seen in the figures, the hinge pin 46 is positioned within and configured to pivot about an axis that is transverse to a longitudinal axis of the patient support structure 14. In addition to pivoting about the axis, the hinge pin 46 can translate within an angled slot 50 in an angled end 52 of the head end member 40. While the angled slot 50 is shown in the head end member 40, it is foreseen that the angled slot 50 may alternatively be positioned in the foot end member 42. In FIGS. 3-4, the patient support structure 14 is in a neutral or horizontal position. In this position, the hinge pin 46 is in a relative midpoint of the angled slot 50. As the patient support structure 14 flexes about the joint 44, the hinge pins 46 pivot and/or translate accordingly such that hip pads 54 move relative to a torso assembly 56 to accommodate the movements of the patient. As will be discussed later and viewing FIG. 3 as a reference, moving from a neutral position to an extension position, the hinge pin 46 rotates counterclockwise and translates to a foot end 58 of the angled slot 50. And, moving from a neutral position to a flexion position, the hinge pin 46 rotates clockwise and translates towards a head end 60 of the angled slot 50. That is, in an extended position, a distance between the torso assembly 56 and the chest pad 54 is greater than the distance between the torso assembly and the chest pad 54 when in a flexed position.

Figure 5:
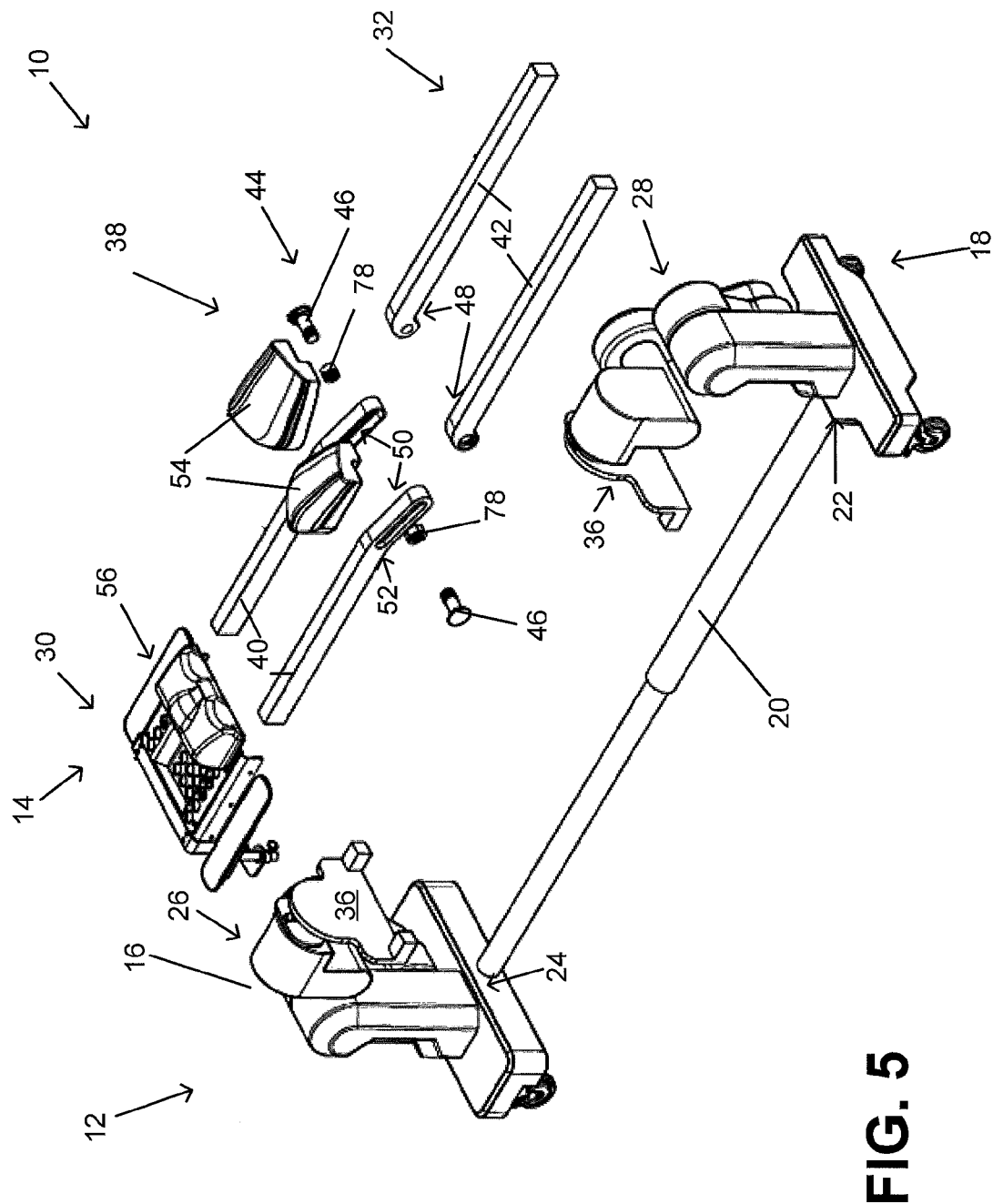
FIG. 5 depicts an exploded top isometric view of the surgical table of FIG. 1.
Figure 6:
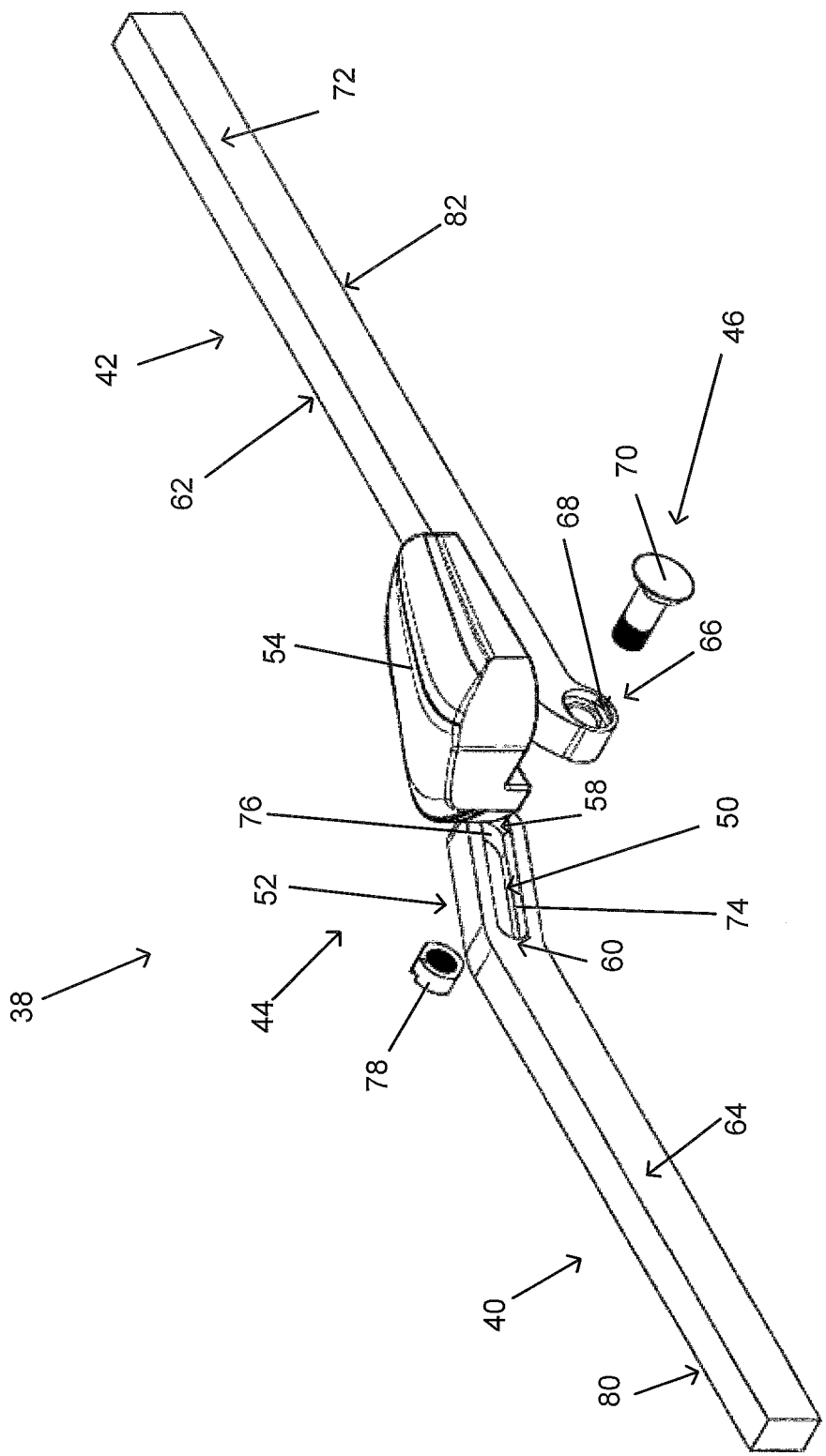
FIG. 6 depicts an exploded top isometric view of a foot end member, a head end member, a hinge pin, and a hip pad.

Moving on, the discussion will focus on the components of the articulating support assembly 38 and FIGS. 5-6, which is are exploded isometric views of the surgical table 10 and an articulating support assembly 38. As seen in FIG. 5, each of the articulating support assemblies 38 is removably coupled with the mounting plate 36. And, each end member 40, 42 is also removably coupled to the mounting plate 36. Positioning of the end members 40, 42 is dependent on forces applied by the articulation assemblies 26, 28 through the mounting plate 36. At a head end section 30 of the patient support structure 14, the torso assembly 56 is removably coupled with the head end members 40 and may be positioned on the head end members 40 relative to the hip pads 54 in a number of positions to either shorten or lengthen a distance that corresponds with the distance between the patient's upper torso and hips. At the foot end section 32 of the patient support structure 14, a sling or other structure (not shown) may be positioned between the respective pair of foot end members 42 to support the lower body limbs of a patient while supported on the surgical table 10. And, while the patient support structure 14 is described with reference to hip pads 54 and a torso assembly 56, the surgical table 10 may include componentry necessary for positioning a patient in a range of positions (e.g., supine, lateral decubitus, among others) where the patient support structure 14 is in a flexion, an extension, or a neutral positioning. For example, the patient support structure 14 may include a flat-top assembly (not shown) instead of the hip pads 54 and torso assembly 56. The flat-top assembly may include a single padded structure that allows for articulation at the joint 44 or the flat-top assembly may include separate respective head end and foot end padded structures that allow for articulation at the joint 44. Additionally, other structures may be used for the flat-top assembly.

Figure 9:
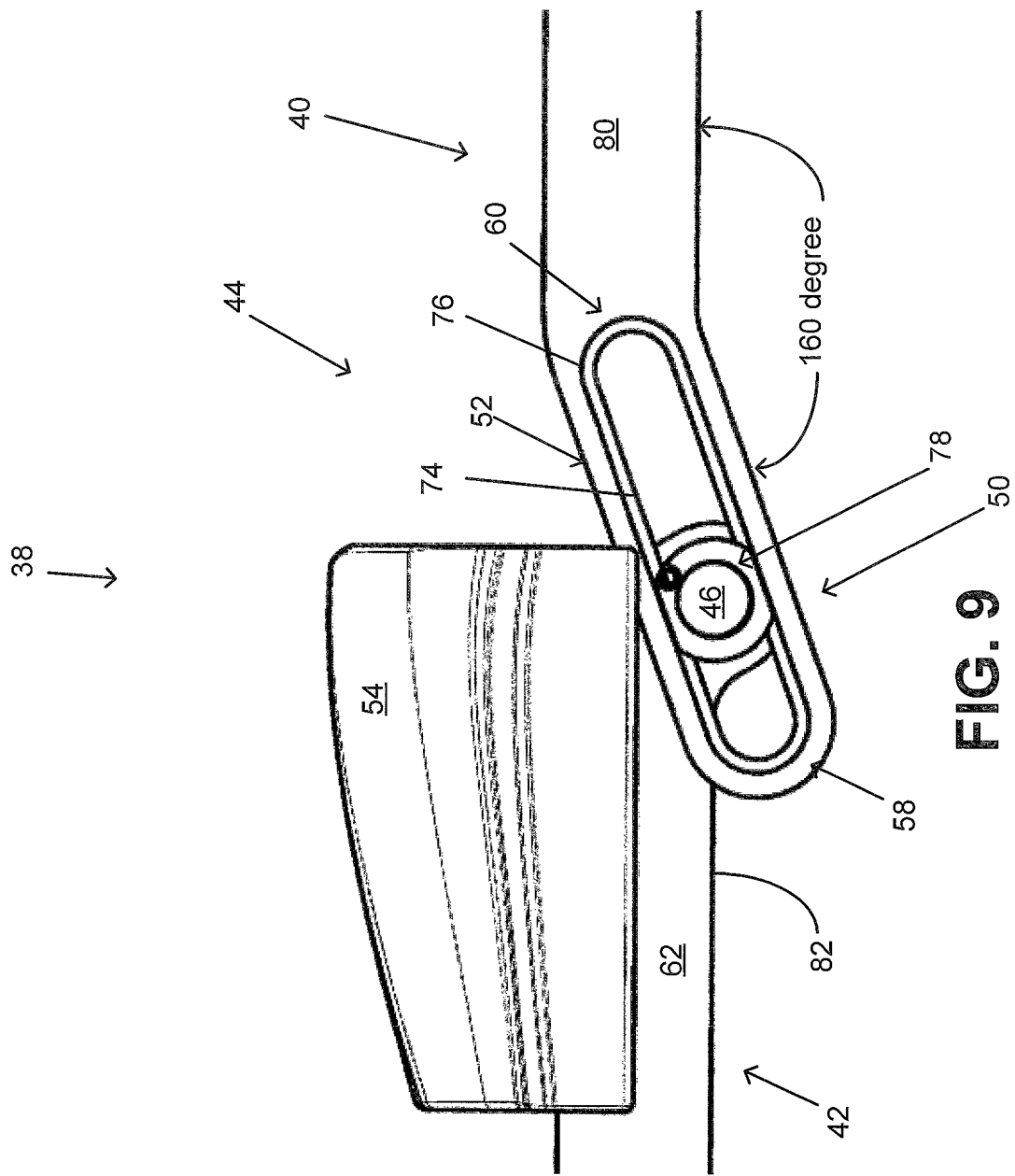
FIG. 9 depicts a close-up side view of the pivoting and translating hinge.

The discussion will now focus on the components and assembly of each articulating support assembly 38. As seen in FIG. 6, the foot end member 42 includes an opening 66 for the hinge pin 46 to extend therethrough. The opening 66 includes a keyed feature 68 such that the hinge pin 46 can only extend therethrough in certain orientations. And, once the hinge pin 46 extends in the opening 66 such that a head 70 of the hinge pin 46 is flush with an outer side 72 of the foot end member 42, the keyed feature 68 limits rotation of the hinge pin 46. To couple the head and foot end members 40, 42 together, an inner side 62 of the foot end member 42 is positioned oppositely to an outer side 64 of the head end member 40 such that the opening 66 in the foot end member 42 is coaxial with a portion of the angled slot 50. The hinge pin 46 is extended through the opening 66 until it is "keyed" with the keyed feature 68. Now, a portion of the hinge pin 46 should protrude through the angled slot 50. As seen in FIGS. 6 and 9, the angled slot 50 includes a small stadium-shaped opening 74 on the outer side 64 of the head end member 40 and a larger stadium-shaped opening 76 on an inner side 80 of the head end member 40. The small stadium-shaped opening 74 is sized slightly larger than a diameter of the hinge pin 46, while the large stadium-shaped opening 76 is sized slightly larger than a nut 78 that is configured to rotationally engage with the hinge pin 46 and couple the respective head and foot end members 40, 42 together. The nut 78 can be any type of nut and will depend on the type of hinge pin 46 used. The nut 78 may be sized such that it can rotate and translate within the large stadium-shaped opening 76 upon articulation of the articulating support assembly 38. To facilitate this movement, the nut 78 may include a bushing in order to provide a smooth bearing surface for rotation and translation within the angled slot 50.

Figure 7:
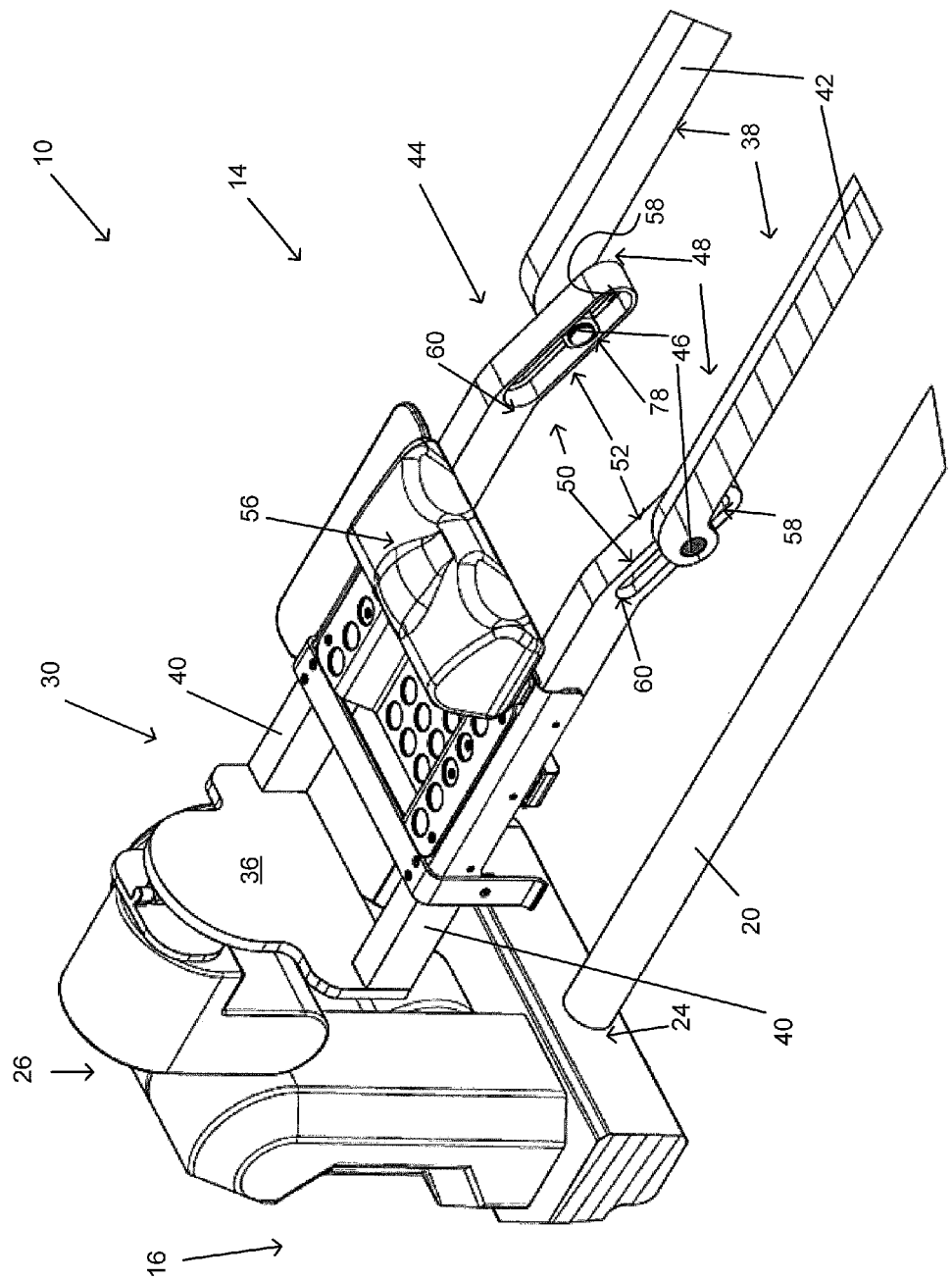
FIG. 7 depicts a top isometric view of the surgical table of FIG. 1 with the foot end members shown in cross-section.
Figure 8:
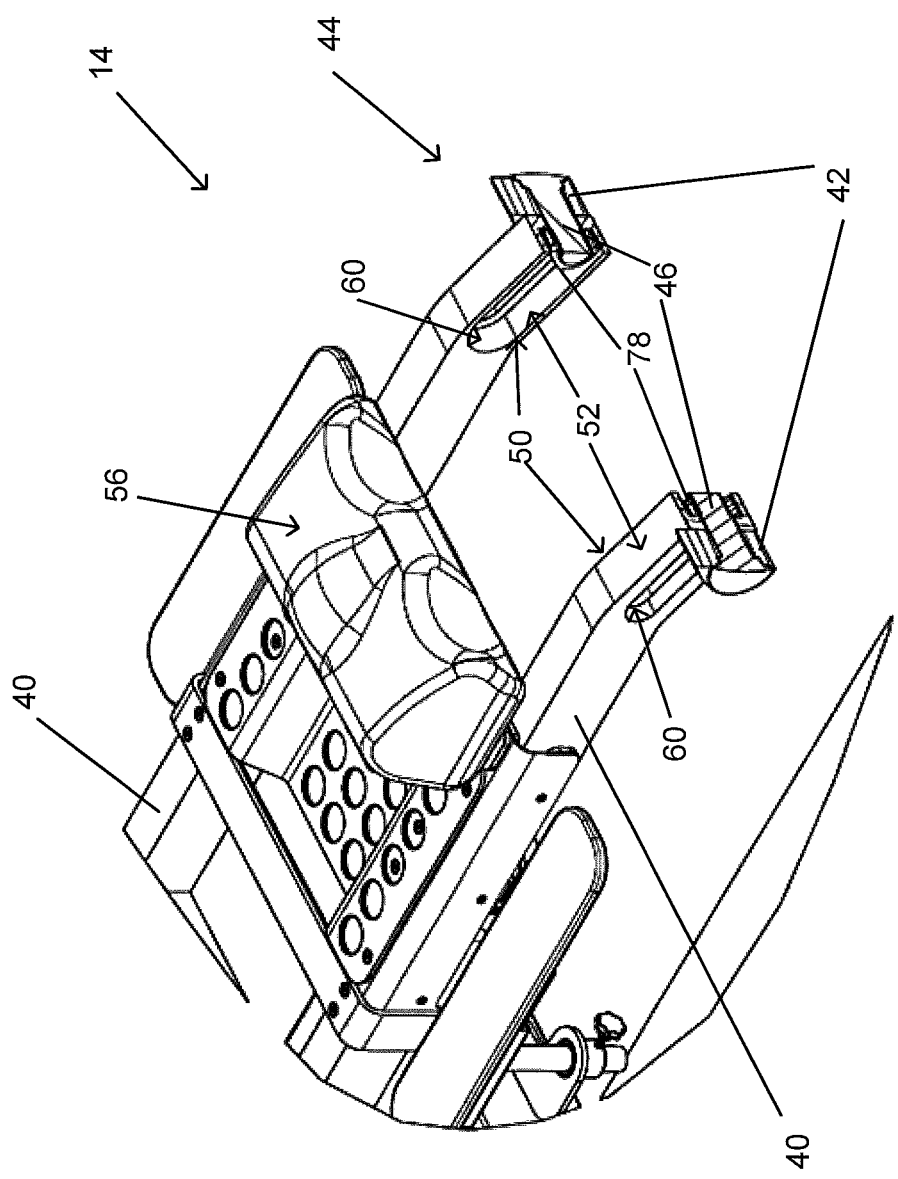
FIG. 8 depicts a cross-sectional view of a hinge pin and a portion of the foot end members and the head end members.

Reference is now made to FIGS. 7-8, which are cross-sectional views of portions of the articulating support assembly 38. FIG. 7 depicts a foot end member 42 in cross-sectional view and it is apparent that the hinge pin 46 extends through the opening 66 in the foot end member 42 and extends through the angled slot 50. FIG. 8 depicts a transverse cross-section of the hinge pin 46, the nut 78, the foot end member 42, and the head end member 40. As seen in this figure, the head end members 40 are coupled on inner sides 62 of the foot end members 42. The nut 78 lies flush with inner sides 80 of the head end members 40 and is sized to pivot and rotate within the angled slot 50.

As seen in FIG. 7, the foot end members 42 are spaced apart a further distance than the head end members 40. That is, an inner side 62 of the foot end member 42 is positioned oppositely to an outer side 64 of the head end member 40 such that the foot end members 42 are spaced further apart than the head end members 40. This may be advantageous for positioning a patient on the table 10 to provide for additional room for the patient's hips and legs to be positioned between and the extend downward (i.e., positioned within a sling) from foot end members 42.

Referring to FIG. 9, which is a close-up view of an internal side of the joint 44, the angled end 52 of the head end member 40 angles downward at about twenty degrees from horizontal. In particular, the slot 50 may include a longitudinal axis extending a length of the slot between the head end 60 of the slot 50 and the foot end 58 of the slot 50. The longitudinal axis may be offset from a longitudinal axis of the head end member 40 by about twenty degrees.

And, the opening 66 in the foot end member 42 define a transverse axis that is about in-line with a bottom side 82 of the foot end member 42. This arrangement of the angled slot 50 and the opening 66 enable the respective ends 40, 42 of the patient support structure 14 to flex in a way that allows for a patient to comfortably and naturally move from a neutral to a flexed or extended position, among other movements.

Figure 10:
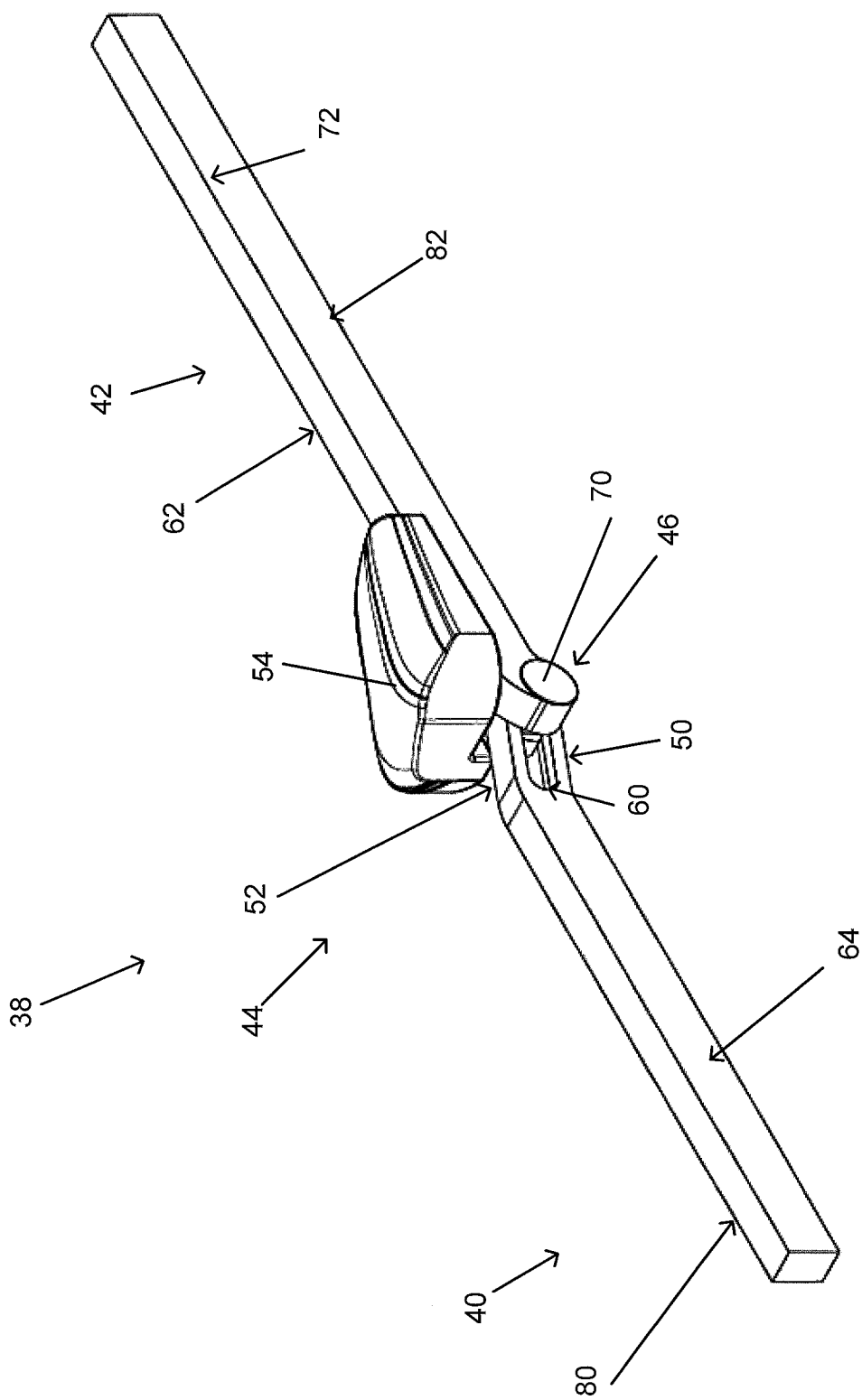
FIG. 10 depicts a top isometric view of the foot end member, the head end member, the hinge pin, and the hip pad of FIG. 9 in assembled form and in a neutral position.
Figure 11:
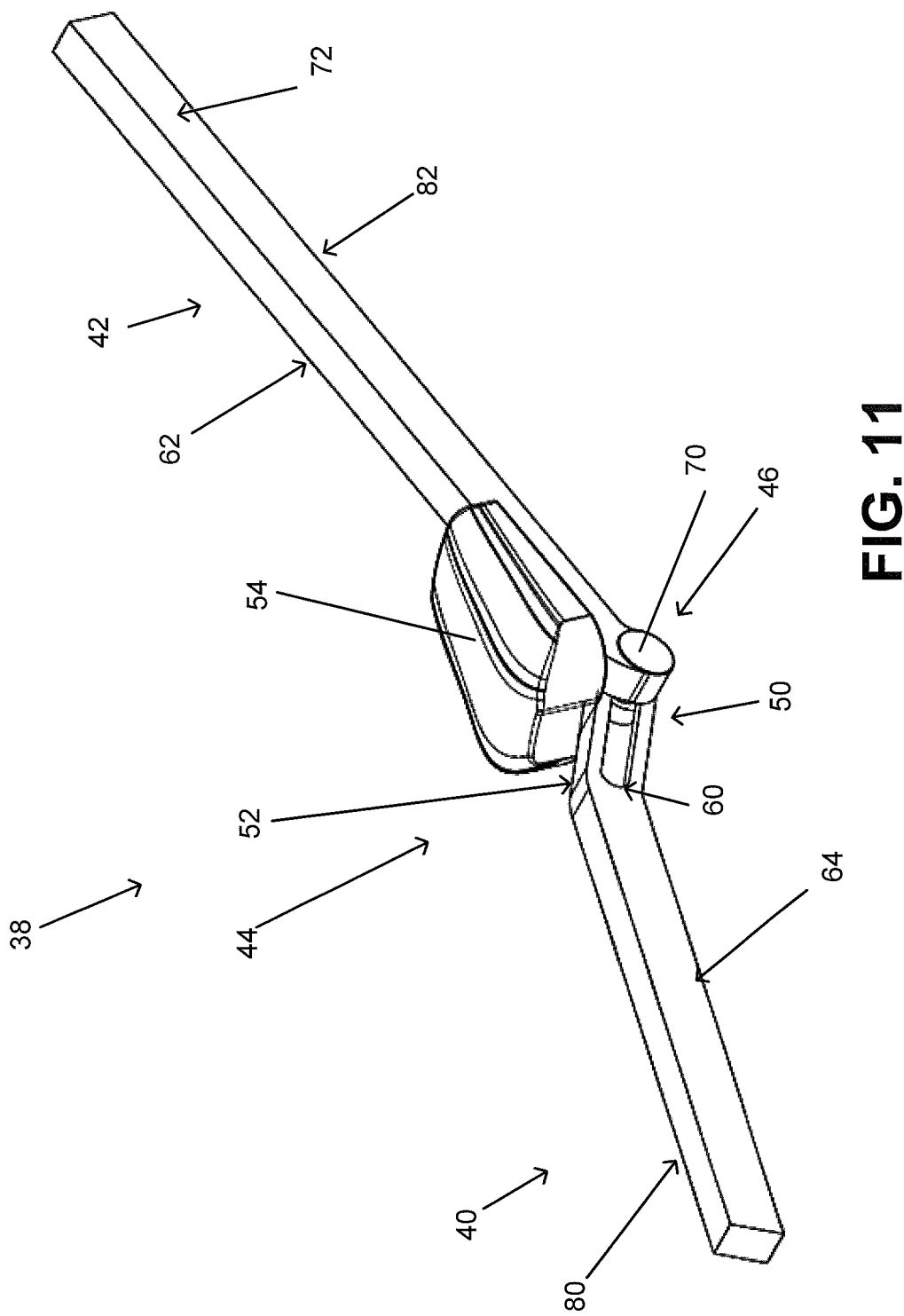
FIG. 11 depicts a top isometric view of the foot end member, the head end member, the hinge pin, and the hip pad of FIG. 9 in assembled form and in an extended position.
Figure 12:
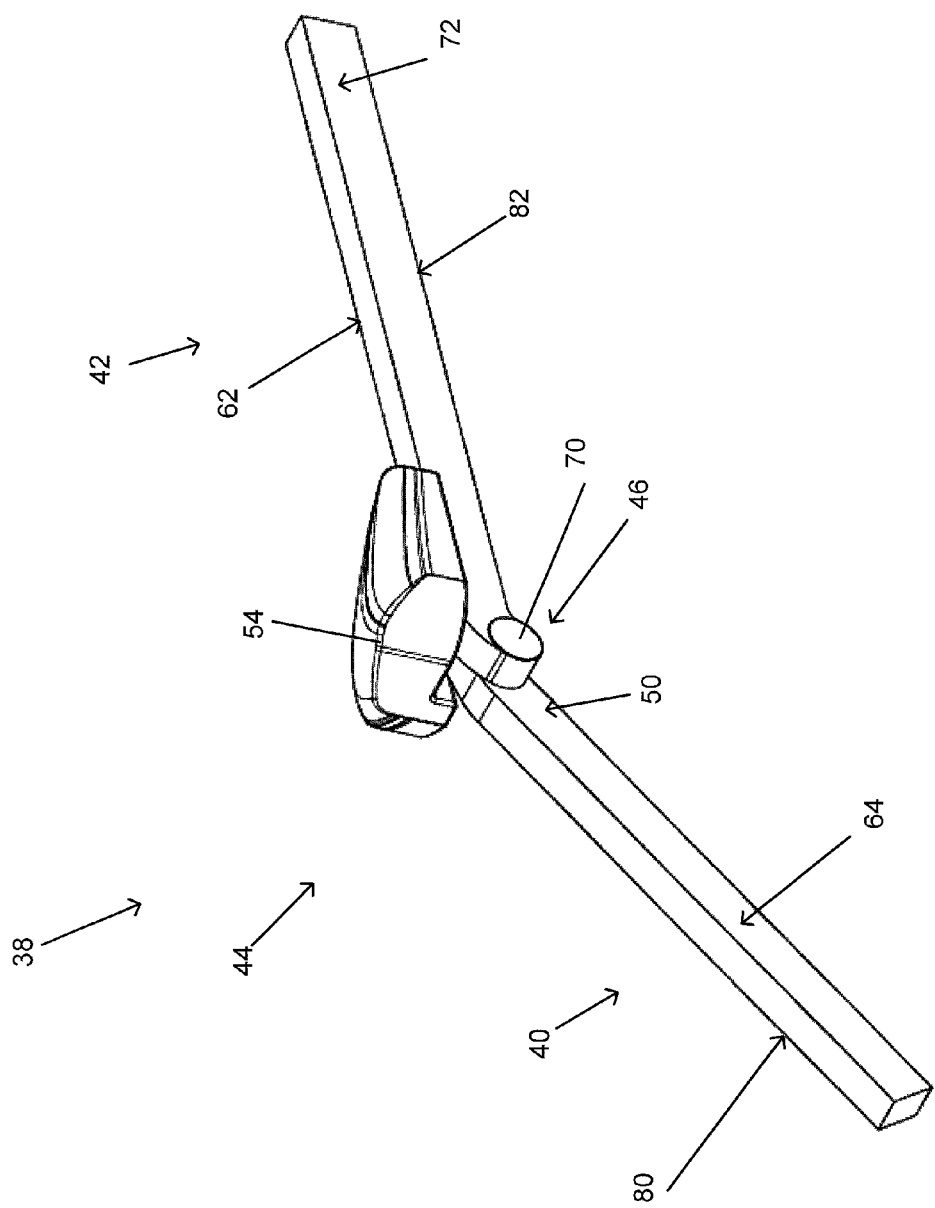
FIG. 12 depicts a top isometric view of the foot end member, the head end member, the hinge pin, and the hip pad of FIG. 9 in assembled form and in a flexed position.
Figure 13:
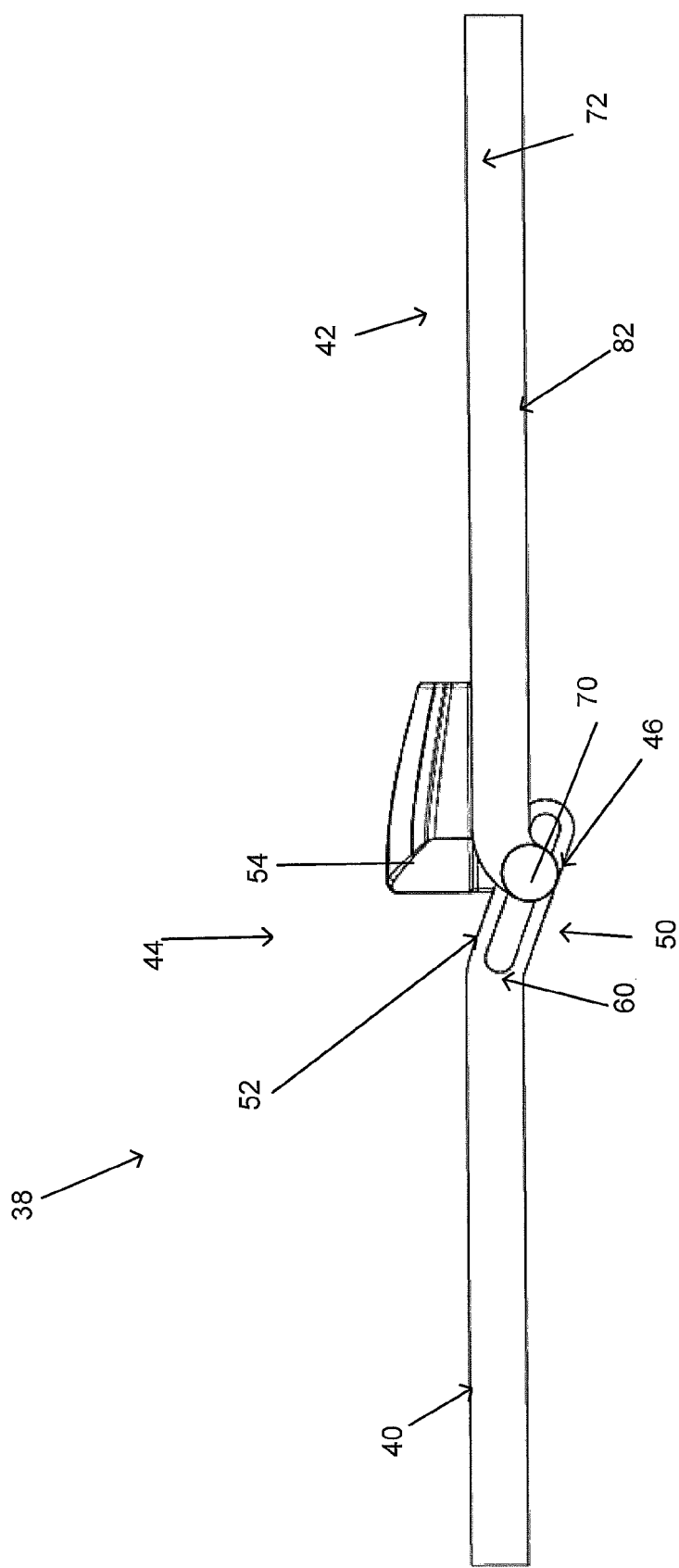
FIG. 13 depicts an outer side view of the foot end member, the head end member, the hinge pin, and the hip pad in a neutral position.
Figure 14:
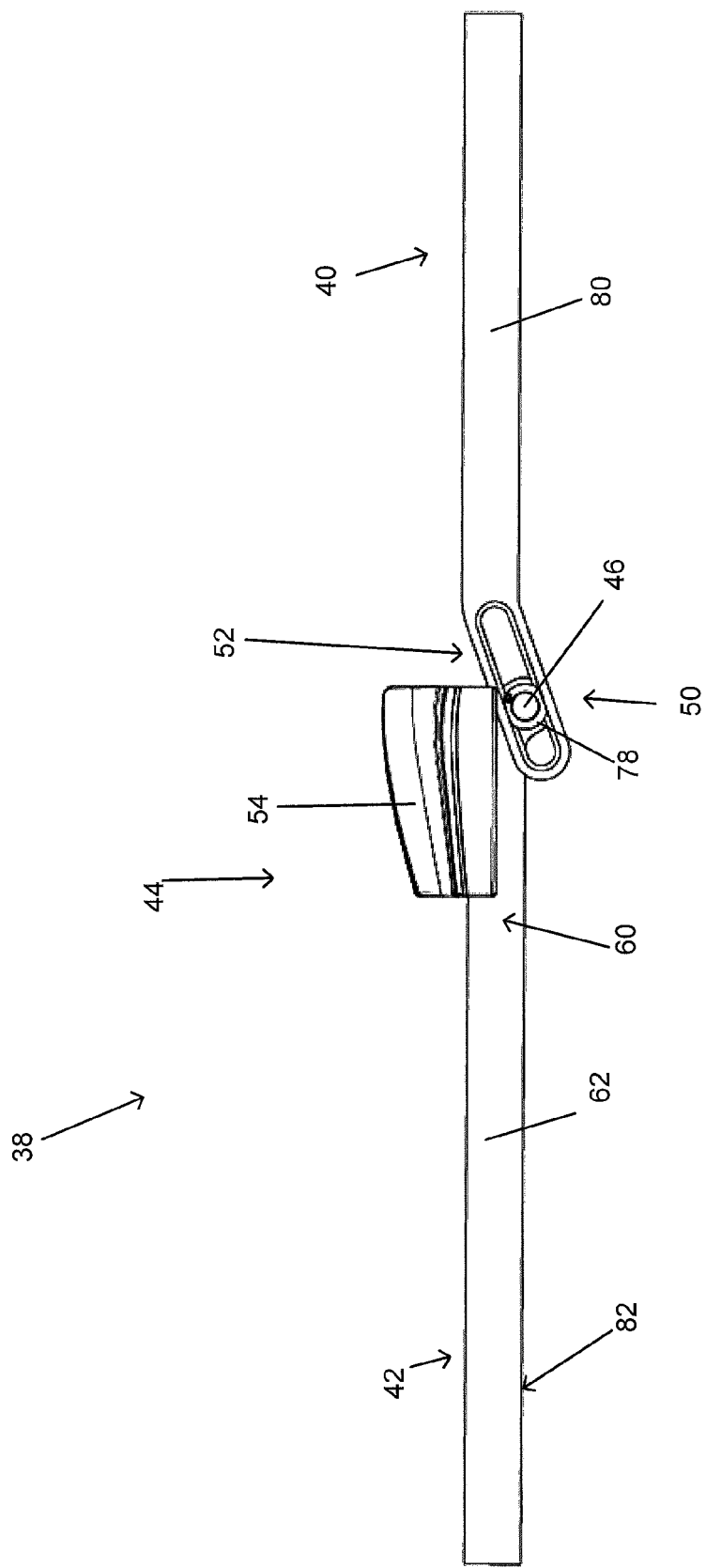
FIG. 14 depicts an inner side view of the foot end member, the head end member, the hinge pin, and the hip pad in a neutral position.
Figure 15:
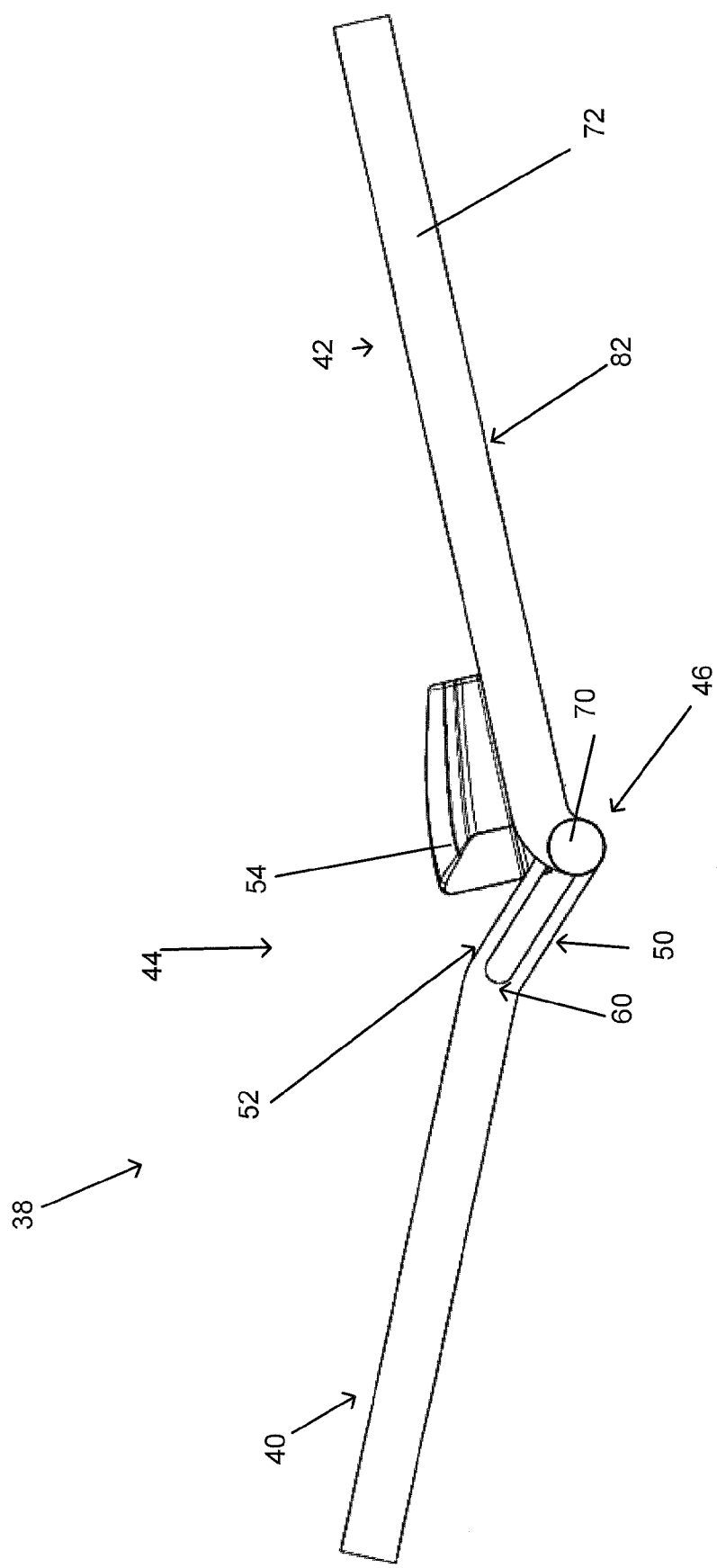
FIG. 15 depicts an outer side view of the foot end member, the head end member, the hinge pin, and the hip pad in an extended position.
Figure 16:
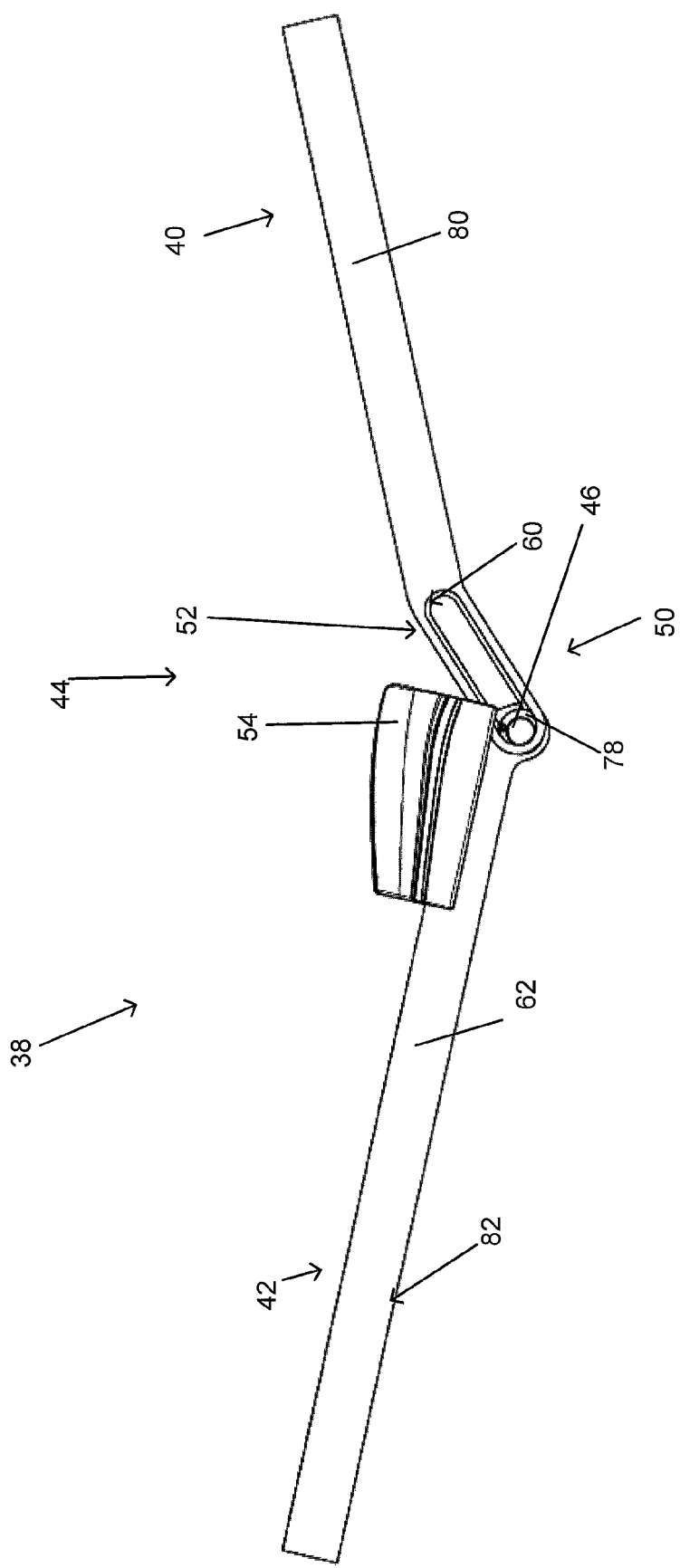
FIG. 16 depicts an inner side view of the foot end member, the head end member, the hinge pin, and the hip pad in an extended position.
Figure 17:
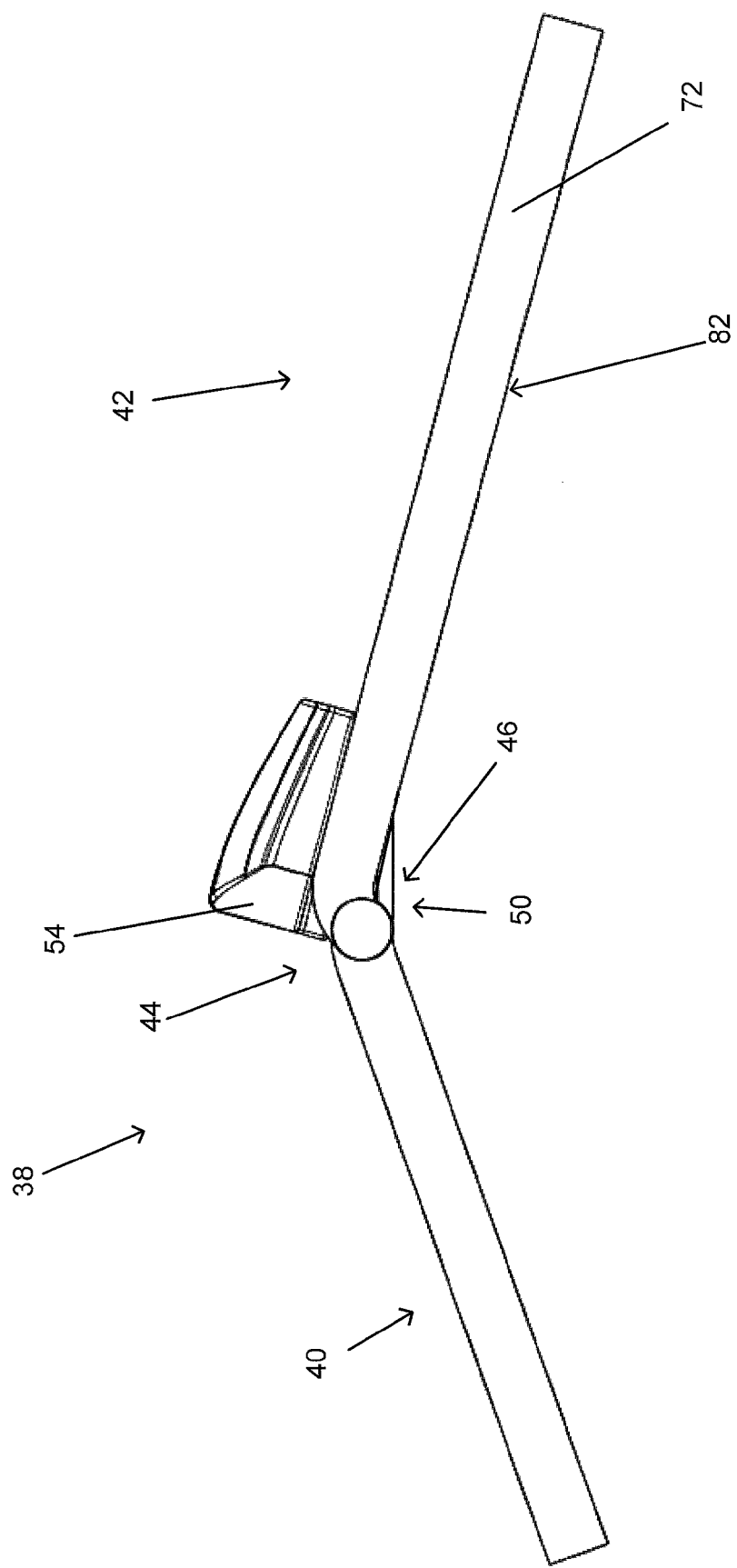
FIG. 17 depicts an outer side view of the foot end member, the head end member, the hinge pin, and the hip pad in a flexed position.
Figure 18:
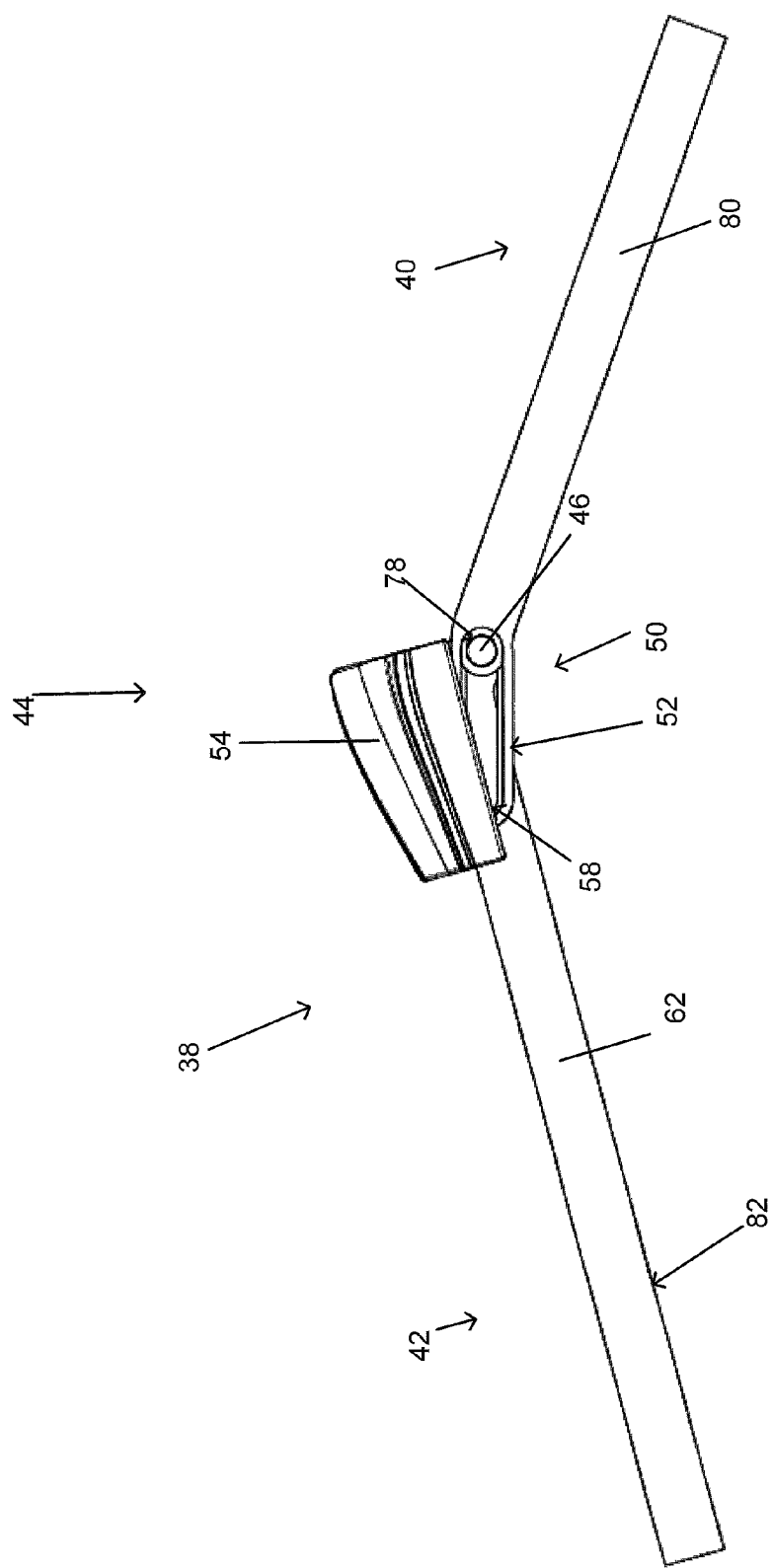
FIG. 18 depicts an inner side view of the foot end member, the head end member, the hinge pin, and the hip pad in a flexed position.
Figure 19:
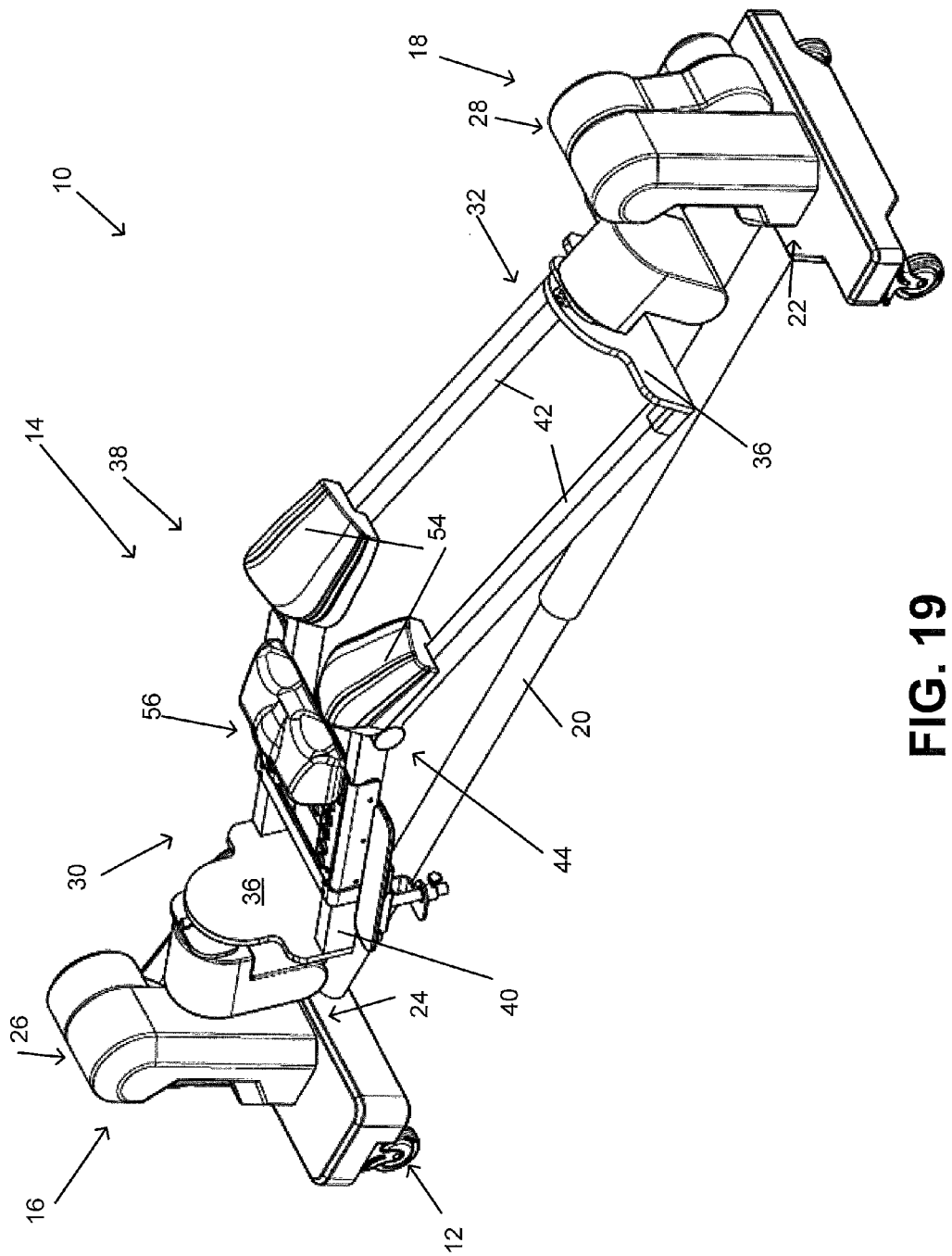
FIG. 19 depicts a top isometric view of the surgical table of FIG. 1 with the patient support structure in a flexed position.
Figure 20:
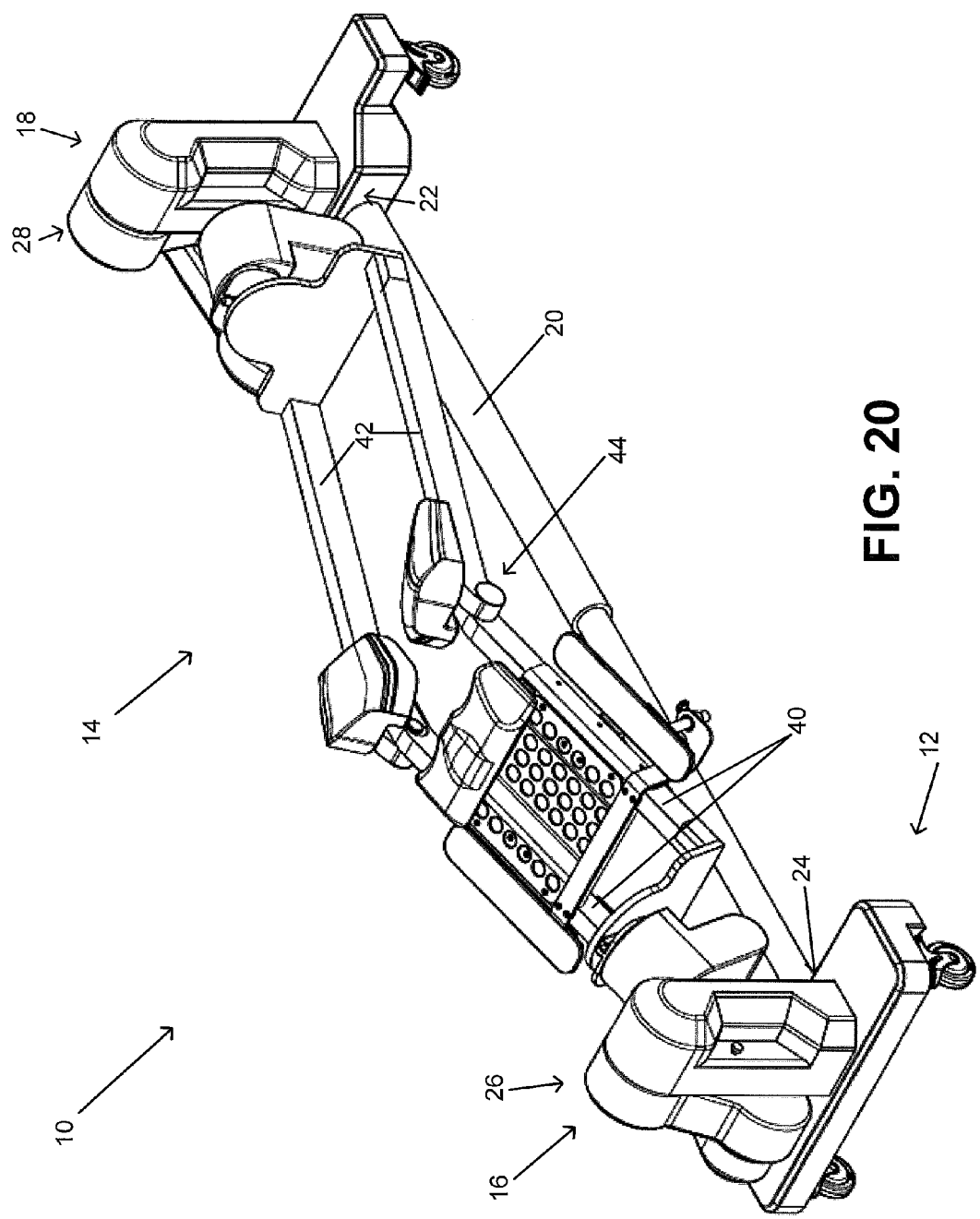
FIG. 20 depicts another top isometric view of the surgical table of FIG. 1 with the patient support structure in a flexed position.
Figure 21:
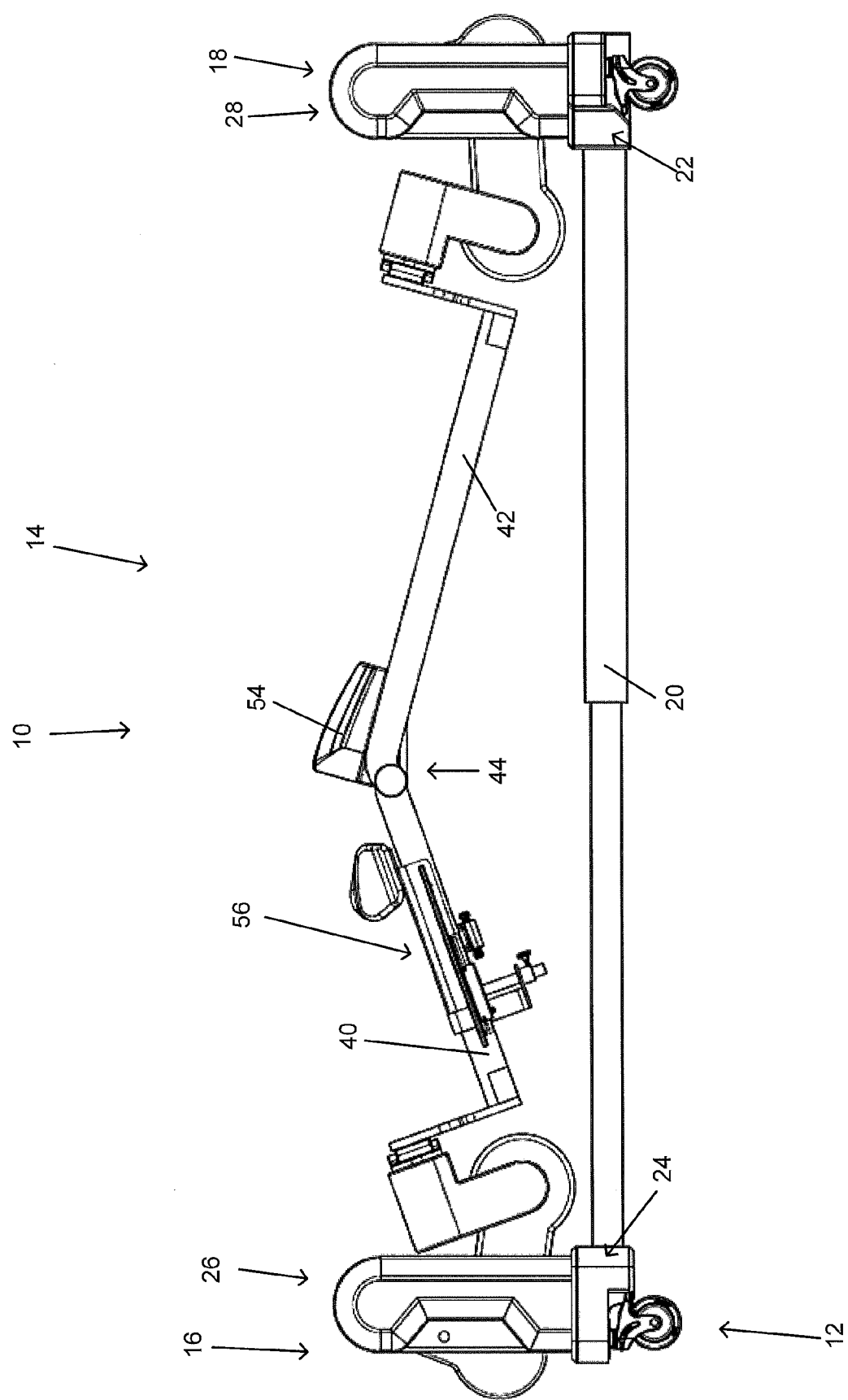
FIG. 21 depicts a first side view of the surgical table of FIG. 1 with the patient support structure in a flexed position.
Figure 22:
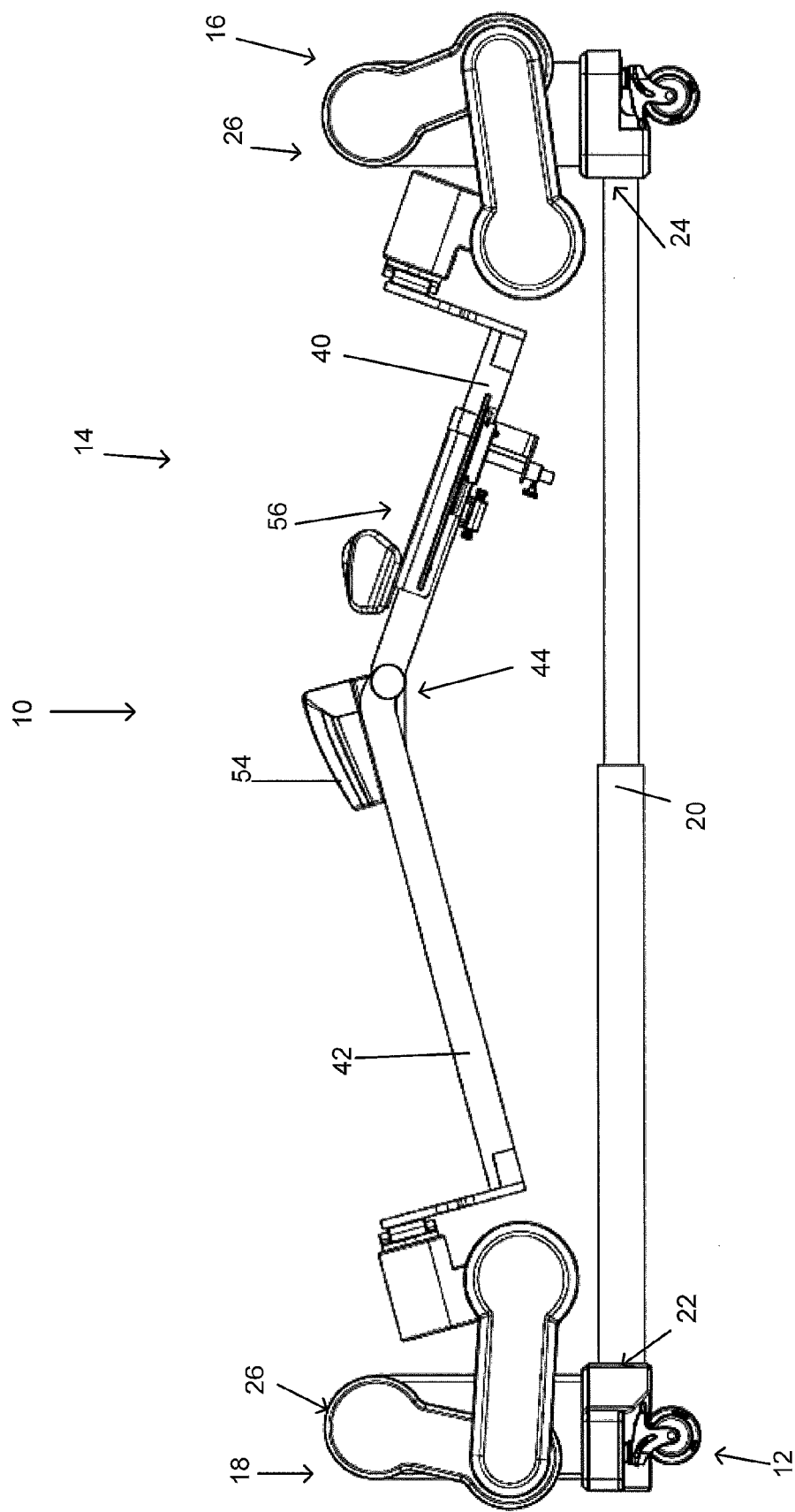
FIG. 22 depicts a second side view of the surgical table of FIG. 1 with the patient support structure in a flexed position.
Figure 23:
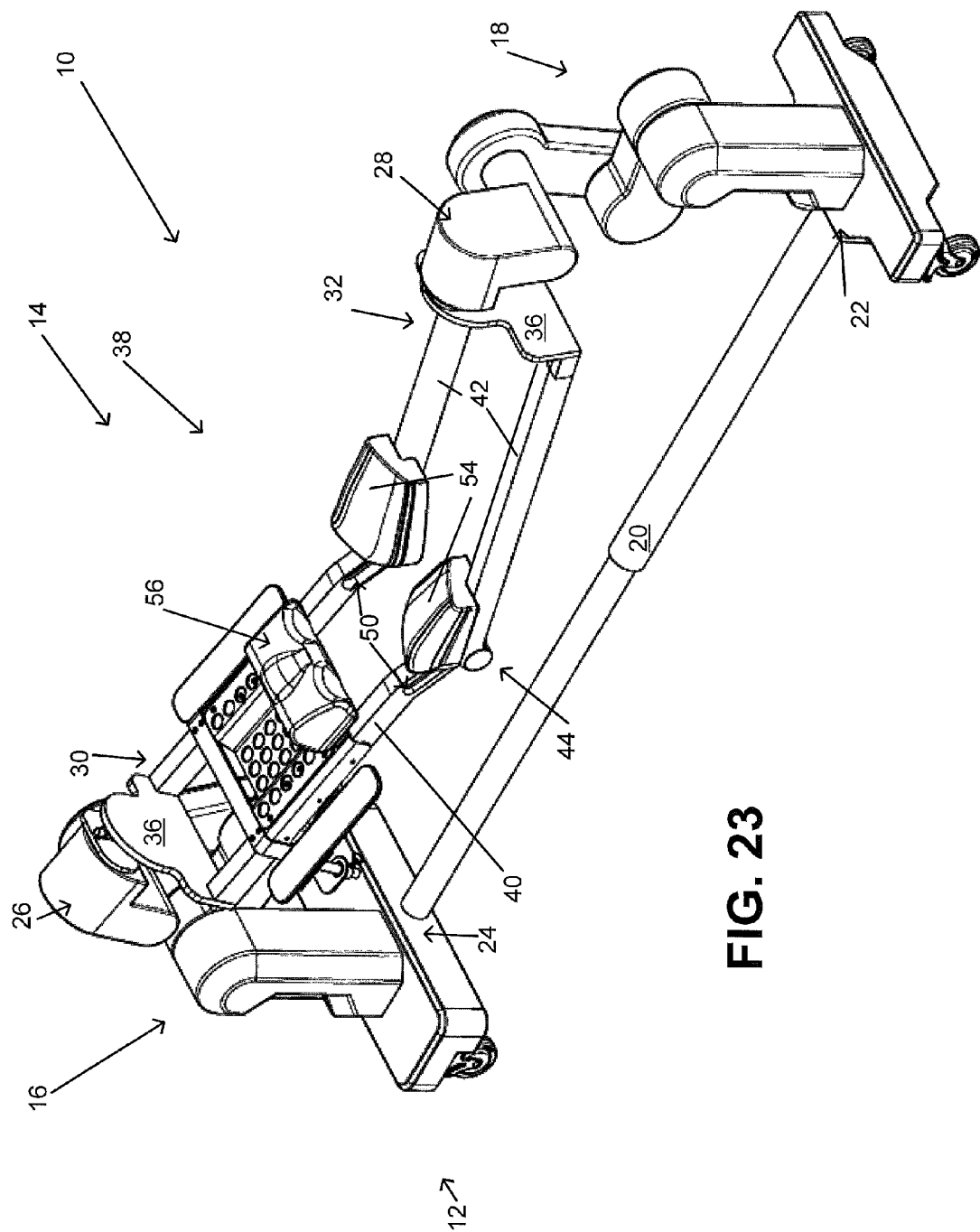
FIG. 23 depicts a top isometric view of the surgical table of FIG. 1 with the patient support structure in an extended position.
Figure 24:
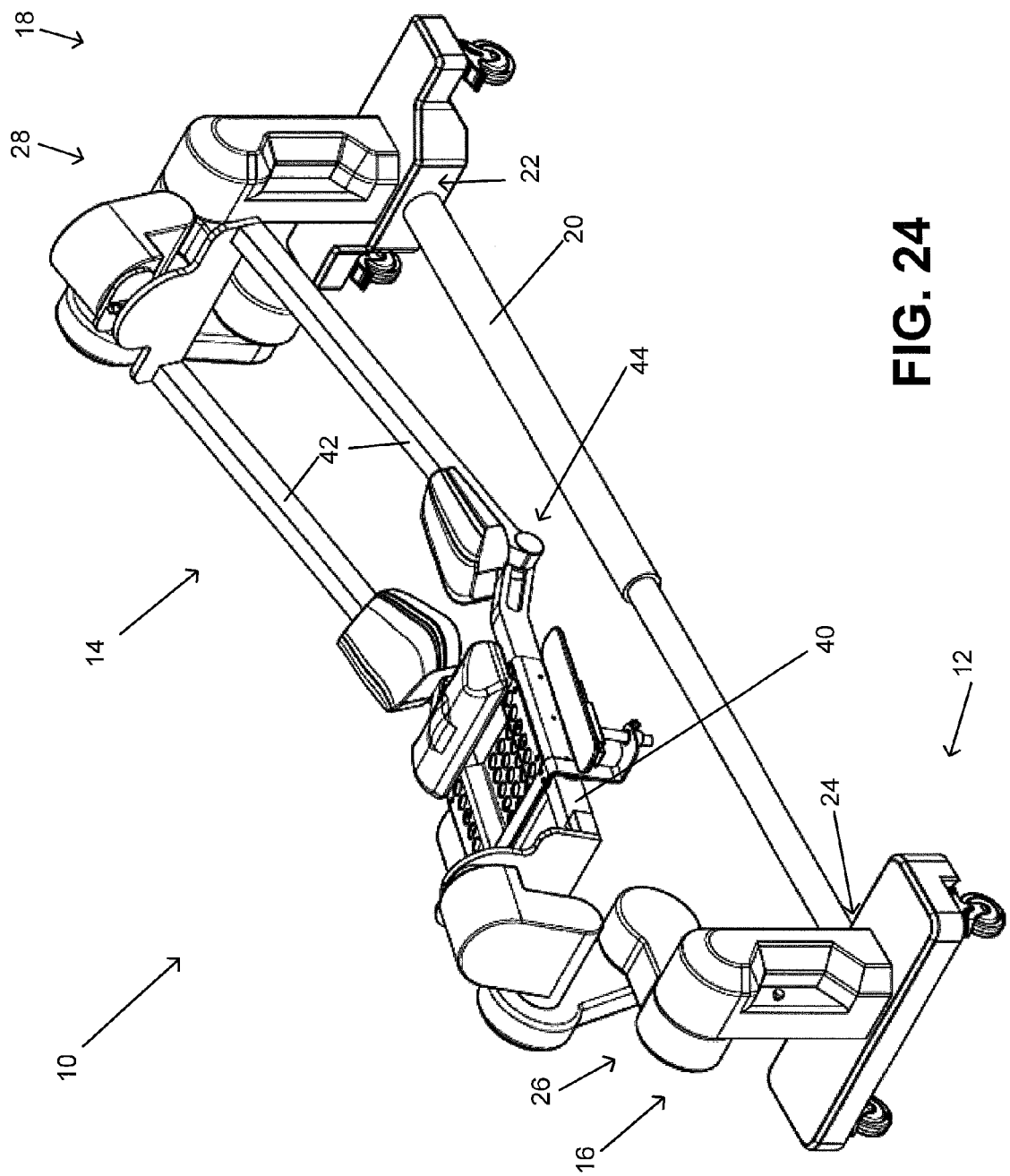
FIG. 24 depicts another top isometric view of the surgical table of FIG. 1 with the patient support structure in an extended position.
Figure 25:
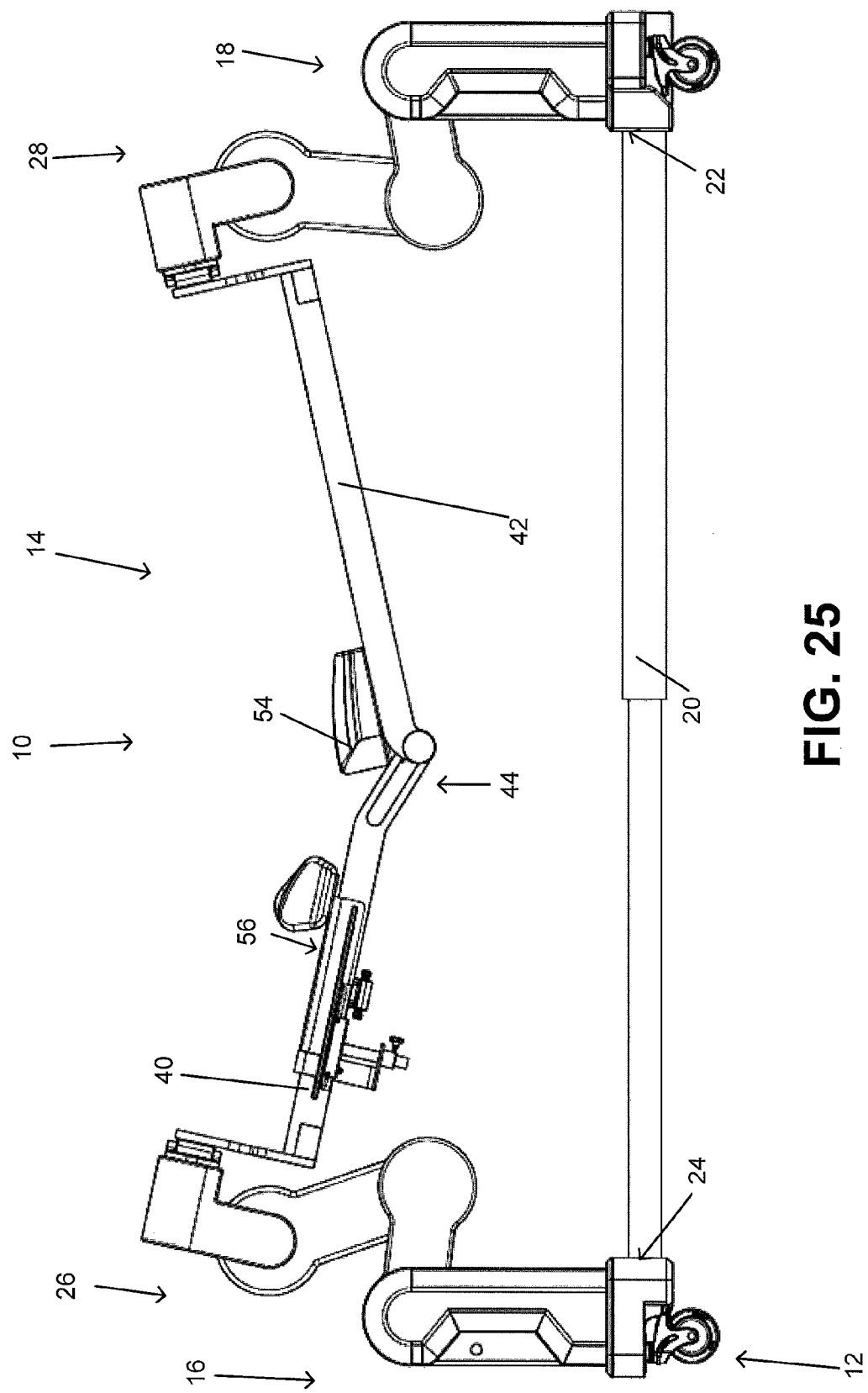
FIG. 25 depicts a first side view of the surgical table of FIG. 1 with the patient support structure in an extended position.

Reference will now be made to FIGS. 10-12, which are top isometric views of the articulating support assembly in a neutral position, an extended position, and a flexed position. FIGS. 13-18 depict similar view as FIGS. 10-12 except the views are from the side. As seen in FIG. 10, in a neutral position, the head and foot end members 40, 42 are generally horizontal. And, in order for the members 40, 42 to be generally horizontal, the hinge pin 46 is positioned generally in a mid-portion of the angled slot. Moving to an extended position from a neutral position, as seen in FIG. 11, the hinge pin 46 rotates counterclockwise and translates toward a foot end 58 of the angled slot 50. This movement may be the result of the coordinated motion of both the foot end and head end articulating assemblies 26, 28, or, this movement may be the result of only one of the assemblies 26, 28. However, in order to articulate the foot end and the head end members 42, 40 the same amount, it may be desirable to drive both articulating assemblies 26, 28. Now referring to FIG. 12, in order to move from a neutral position to a flexed position, the hinge pin 46 rotates clockwise and translates towards a head end 60 of the angled slot. Similarly as to previously described, this movement may be the result of driving one or both articulating assemblies 26, 28. However, in order to articulate the members 40, 42 the same amount, it may be desirable to drive both assemblies 26, 28.

Figure 33A:
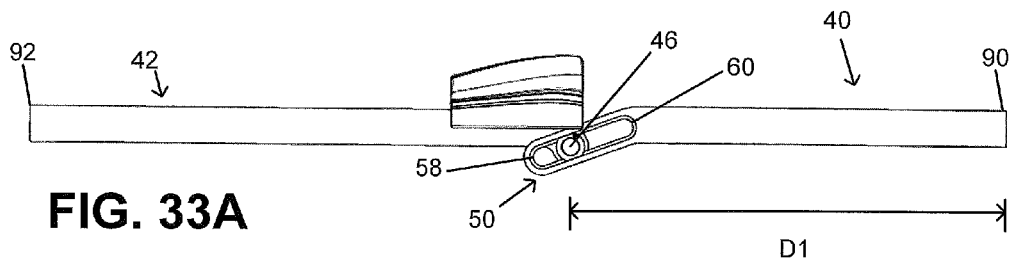
FIGS. 33A-33C depict side views of the head and foot end members in a neutral position, an extended position, and a flexed position, respectively.
Figure 33B:
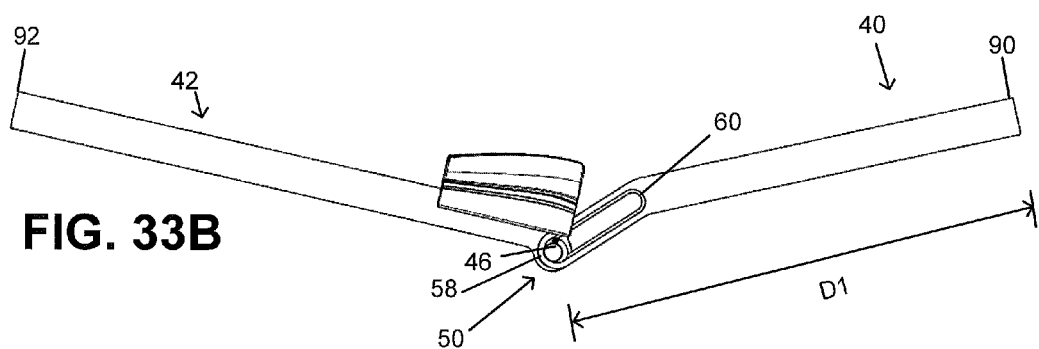
Figure 33C:
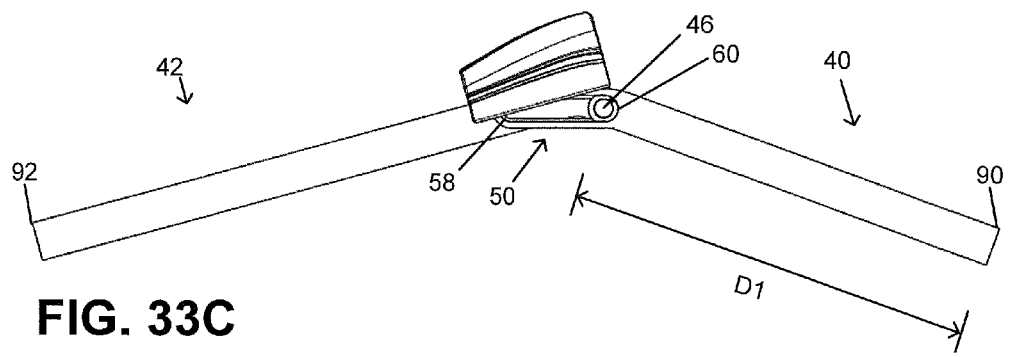

Turning to FIGS. 33A-33C, which are side views of the head and foot end members 40, 42 in a neutral position, an extended position, and a flexed position, respectively, a distance D1 between the hinge pin 46 and outer ends 90 (i.e., where the members 40 coupled with the mounting plate 36) of the head end members 40 may increase or decrease when the head end members 40 and the foot end members 40 articulate relative to each other about the hinge pin 46. Additionally, another distance between the hinge pin 46 and the outer ends 92 of the foot end members 42 may remain substantially or completely constant when the head end members 40 and the foot end members 42 articulate relative to each other about the hinge pin 46.

More specifically, moving from a neutral position to an extended position lengthens the patient support structure 14 by effectively lengthening the distance D1 of the head end member 40 from the head end section 30 of the patient support structure 14, or a torso assembly positioned thereon, to the hinge pin 46. And, moving from a neutral position to a flexed position shortens the patient support structure 14 by effectively shortening the distance D1 of the head end member 40 from the head end section 30 of the patient support structure 14, or a torso assembly positioned thereon, to the hinge pin 46. The effective lengthening and shortening of the distance D1 of the head end member 40 corresponds to a natural movement of the patient's torso during flexion and extension. That is, when a patient moves from a neutral position to an extended position, the torso is lengthened and when a patient moves from a neutral position to a flexed position, the torso is shortened.

Still referring to FIGS. 33A-33C, it is also noted that when the hinge pin 46 is positionally located in between the head end 60 of the slot 50 and the foot end 58 of the slot 50, the head and foot end members 40, 42 are in a neutral position, which means the head and foot end members 40, 42 are substantially parallel, as seen in FIGS. 33A, 10, and 13-14, for example. In this and other instances, substantially parallel may mean exactly parallel, within a few degrees of parallel, or generally parallel.

When the patient support structure 14 moves from the neutral position to an extended position, as shown in FIG. 33B, the hinge pin 46 moves towards a foot end 58 of the slot 50. Conversely, when the patient support structure 14 moves from the neutral position to a flexed position, as shown in FIG. 33C, the hinge pin 46 moves towards a head end 60 of the slot 50. An extended position, as shown in FIGS. 33B, 11, and 15-16, for example, may be defined as when a topside angle of the patient support structure 14 (i.e., between opposing head and foot end members 40, 42 about the hinge 44) is less than one hundred eighty degrees. The topside is defined as opposite the floor or base assembly 12, which is positioned on a bottom side of the patient support structure 14. A flexed position, on the other hand, and as shown in FIGS. 33C, 12, and 17-18, for example, may be defined as when a topside angle of the patient support structure 14 is greater than one hundred eighty degrees.

While the present disclosure discusses a pivoting and translating hinge having a hinge pin 46 fitting within an angled slot 50, the hinge may be differently configured while still being within the scope of the present disclosure. It is foreseen that the hinge may be a bearing or roller mechanism that includes a track and a moveable bearing block that translates on the track. Other mechanisms are possible that adjust a position of a hinge axis and effectively shortens and lengthens a distance D1 between the ends 90 of the head end member 40 and the hinge axis, which is shown by the hinge pin 46 in the present embodiments.

The effective lengthening and shortening of the head end member 40 is desirable to replace the trunk translation previously provided by a trunk translator mechanism linked in some way to a chest slide. To illustrate, when a patient's torso and pelvis are manipulated from a neutral position to an extended position, for example, the pelvis must rotate around the hips, wherein the top of the sacrum gets closer to the trunk region while the lumbar spine increases its lordosis. The torso must either move away from the sacrum and pelvis in a cephalad direction, which is undesirable as it moves the patient towards anesthesia equipment, or the pelvis can move caudad, which is more desirable. It is preferable for the torso, including the patient's head, to not move positions while the patient support structure 14 articulates about the joint 44 so that access to the patient's upper body is undisturbed. This is better for anesthesia and the safety of the patient under a general anesthesia. If this type of movement does not occur, the lumbar spine can undergo unwanted compression, which can be harmful, especially to neurologic structures.

When a patient's torso and pelvis are manipulated into flexion, the pelvis must rotate considerably around the hips in an opposite direction from that of extension described above. To avoid unwanted distraction of the lumbar spine, either the torso and head must move or the pelvis must move cephalad leaving the torso and head unchanged in position with respect to the head end section 30 of the patient support structure 14 and relative to personnel providing anesthesia. In this way, the distance between fixed points on the chest and pelvic pads remains substantially constant and unchanging with full flexion and extension of the patient support structure 14 at its inward articulation at the joint 44.

The exact length of the angled slot 50, angle of the angle slot 50, and amount of translation during the movements described above may change based upon a patient's size or a size of the components of the surgical table 10, among other variables. In certain implementations, the angled slot may include a length of about 9 inches, and may include a translational movement of about 4 inches when moving from a neutral position to an extended position of about thirty degrees. And, the angled slot 50 may include a translational movement of about 5 inches when moving from a neutral position to a flexed position of about forty degrees.

Moving on, reference is now made to FIGS. 19-26, which depict various views of the surgical table 10 with the patient support structure 14 in flexion and extension. In particular, FIGS. 19-22 depict the patient support structure 14 in flexion where the head end and foot end articulation assemblies 26, 28 are generally elevated the same amount, but the translation of the foot end articulation assembly 28 is extended further from the foot end support column 18 than the head end articulation assembly 26 is extended from the head end support column 16. And, the roll axes extending perpendicularly from the mounting plates 36 are not coaxially aligned and the foot end members 42 have been moved caudad. FIGS. 23-26, on the other hand, depict the patient support structure 14 in extension where the head end and the foot end articulation assemblies 26, 28 are generally elevated the same amount, but the translation of the foot end articulation assembly 28 is extended further from the foot end support column 18 than the head end articulation assembly 26 is extended from the head end support column 16. And, the roll axes extending perpendicularly from the mounting plates 36 are not coaxially aligned and the foot end members 42 have been moved cephalad. While the previously described figures included certain orientations of the articulation assemblies 26, 28, other arrangements are possible to flex the patient support structure 14 in flexion and extension and are, thus, contemplated by this disclosure.

Figure 26:
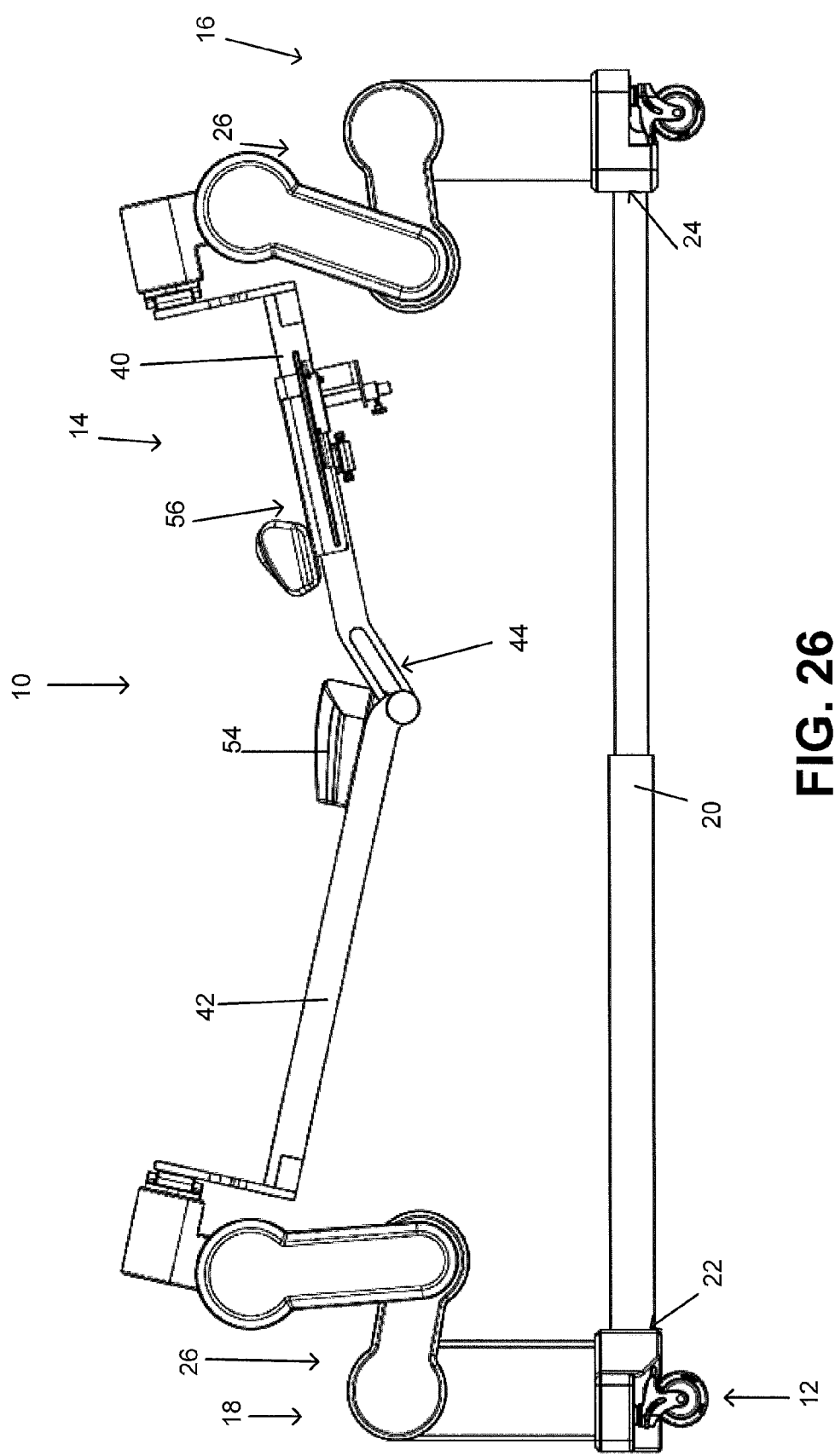
FIG. 26 depicts a second side view of the surgical table of FIG. 1 with the patient support structure in an extended position.
Figure 27:
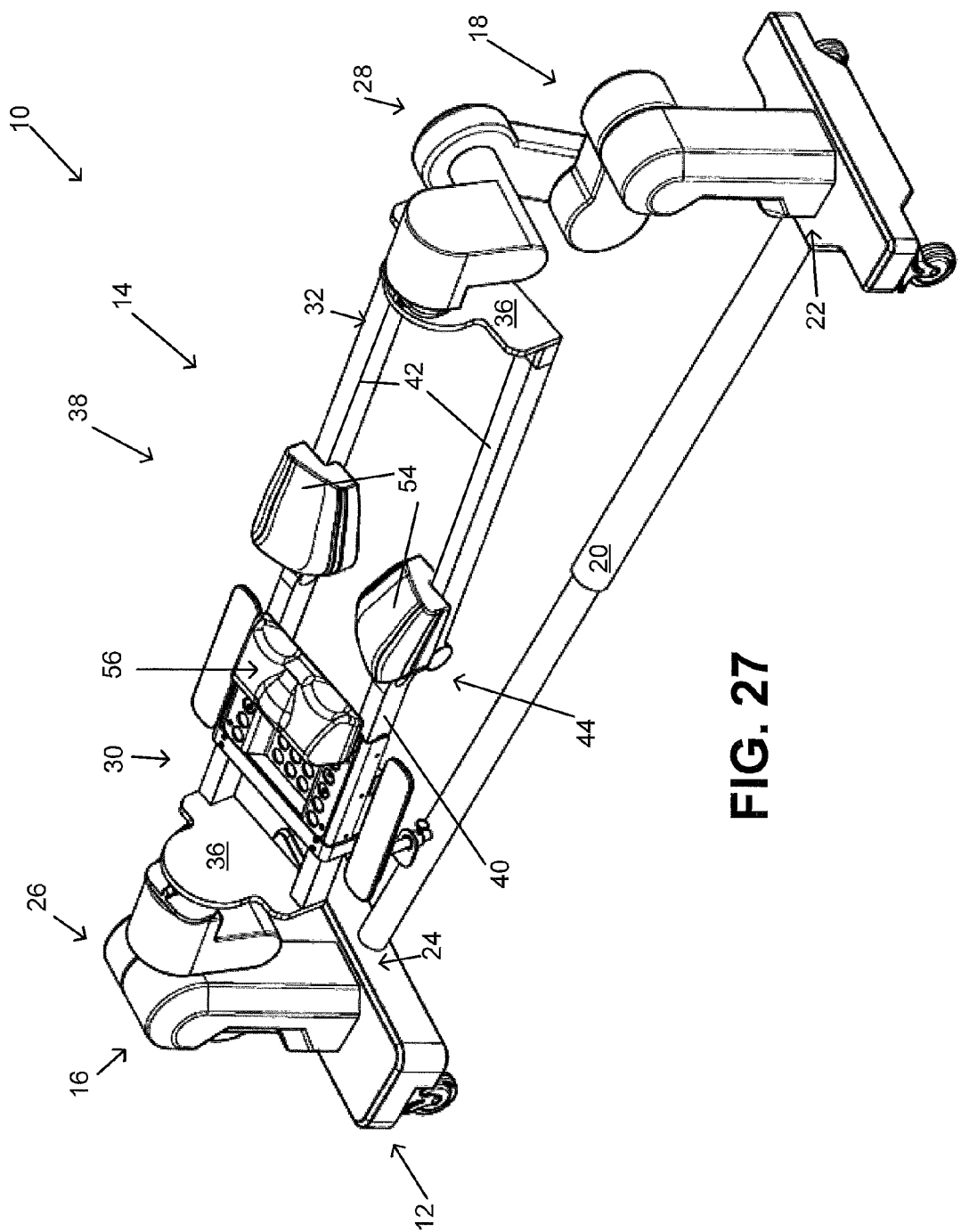
FIG. 27 depicts a top isometric view of the surgical table of FIG. 1 with the patient support structure in a roll.
Figure 28:
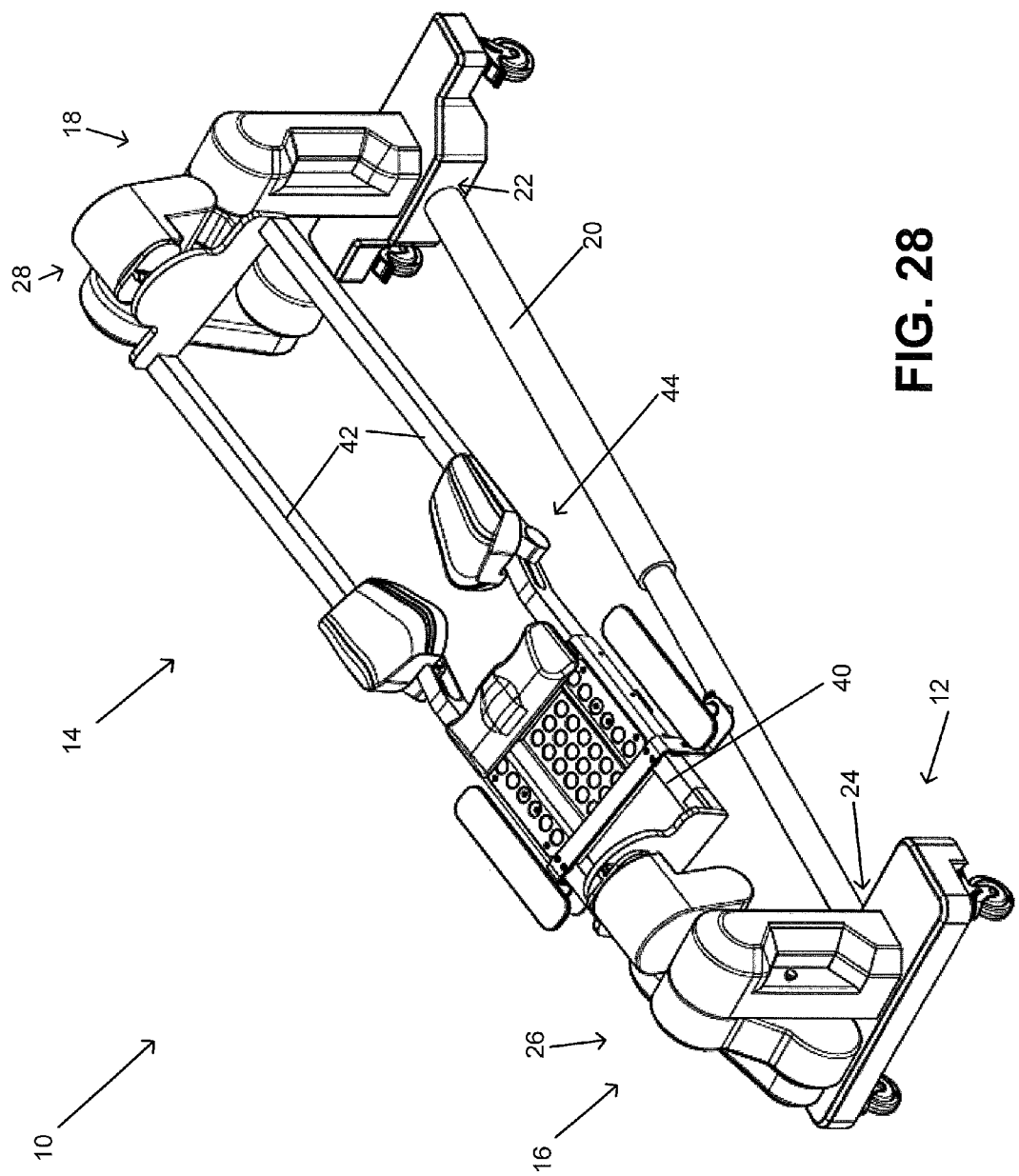
FIG. 28 depicts another top isometric view of the surgical table of FIG. 1 with the patient support structure in a roll.
Figure 29:
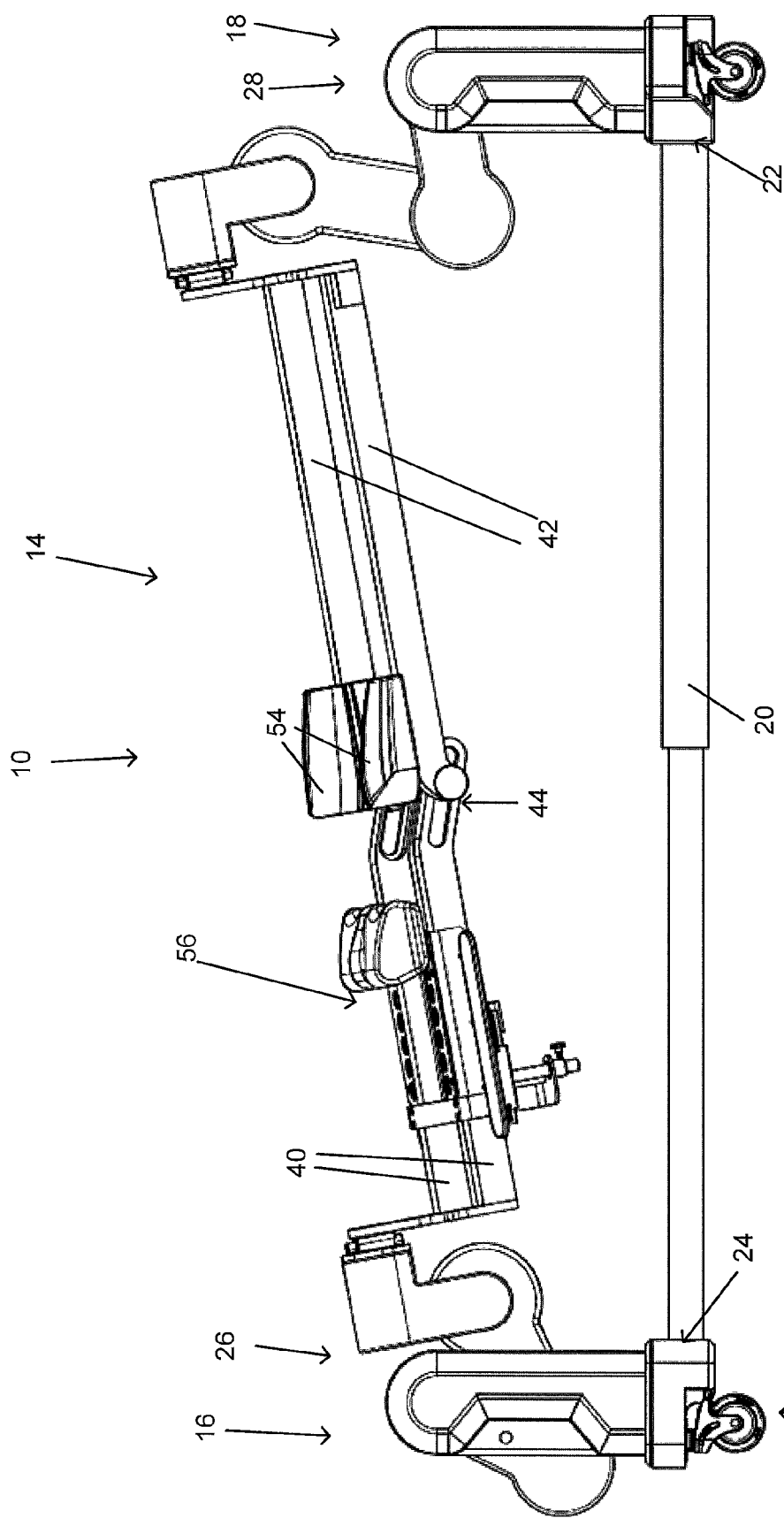
FIG. 29 depicts a first side view of the surgical table of FIG. 1 with the patient support structure in a roll.
Figure 30:
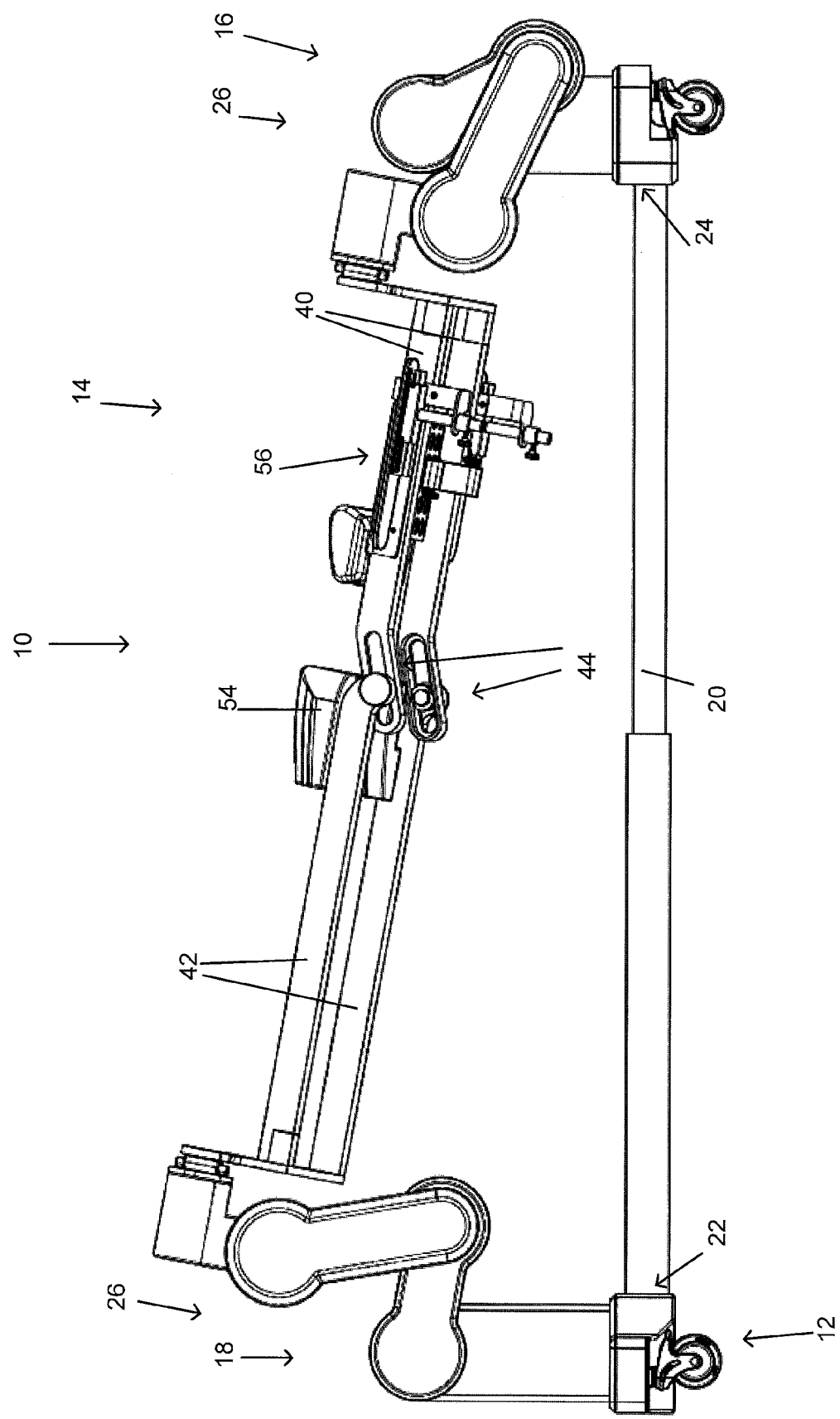
FIG. 30 depicts a second side view of the surgical table of FIG. 1 with the patient support structure in a roll.
Figure 31:
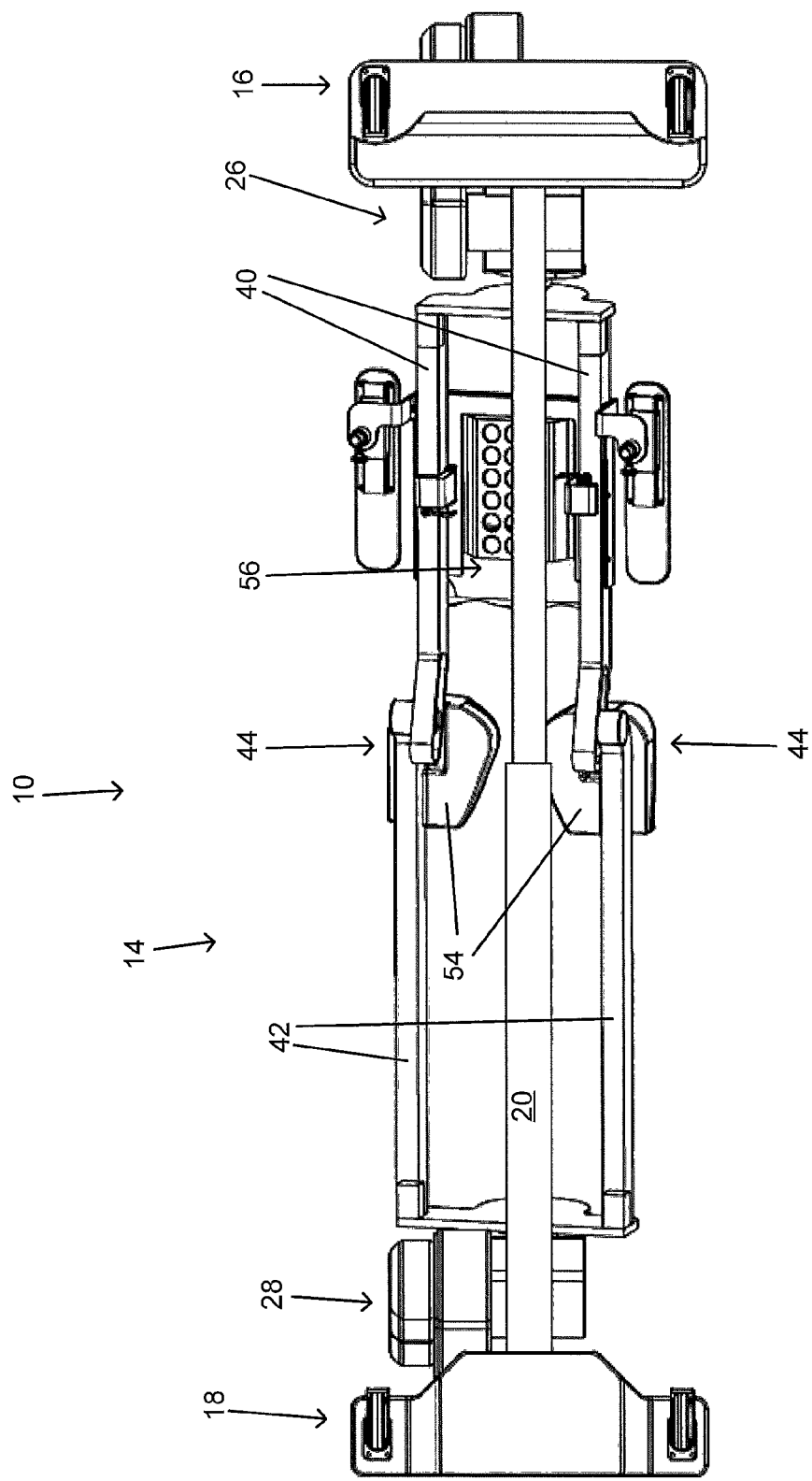
FIG. 31 depicts a bottom view of the surgical table of FIG. 1 with the patient support structure in a roll.

In the previously described figures, the roll axes were not coaxially aligned. Turning to FIGS. 27-31, which are various views of the surgical table 10 with the patient support structure 14 in a roll, it can be seen that the roll axes are coaxially aligned. With hinge pin 46 free to pivot and translate within the angled slot 50, roll or tilting around the longitudinal axis may be accomplished by driving/controlling both the head end and foot end articulation assemblies 26, 28. In particular, it may be beneficial to actively control the rotation around the yaw axis and transverse translation of the head and foot ends 30, 32 of the patient support structure 14 during roll or rotation around the longitudinal axis. Such active control over rotation around the yaw axis and transverse translation by the head end and foot end articulation assemblies 26, 28 may keep the respective head end and foot end members 40, 42 from binding laterally at the joint 44. In particular and in certain implementations without active control (i.e., passive control) over yaw rotation, the head and foot end members 40, 42 may not remain parallel at the joint 44, thus, subjecting the hinge pin 46 to shearing forces that could inhibit movement within the angled slot 50 and perhaps damage the hinge pin 46. On the other hand, with active control over yaw rotation and transverse translation, the head and foot end members 40, 42 may maintain a parallel orientation and may maintain the hinge pin 46 in a constant state with respect to applied forces (i.e., except for the force of gravity) during a roll or tilt and, thus, prevent binding in the joint 44. While active control of the yaw rotation and transverse travel is described with reference to FIGS. 27-31, such control is applicable to other orientations of the surgical table 10. In FIG. 26, for example, the roll axes are not aligned, but with powered yaw and transverse travel, the patient support structure 14 may facilitate a roll or tilt.

While there is potential to bind the joint at the hinge pin 46 in certain implementations without active control over the yaw rotation and transverse translation, modifications to the assembly may be possible to mitigate the potential for binding such that yaw rotation and transverse translation may be controlled passively with less than both articulation assemblies 26, 28 providing active control. Regardless of the powered nature of the articulation assemblies 26, 28 it is noted that the base assembly 12 provides for a roll axis that is above the patient support structure 14. Such a roll axis is desirable because it is safer and more comfortable for the patient.

Regarding the motors that are mentioned in reference to the articulation assemblies 26, 28, among other motors to be described, the motors may be any type of rotary actuator. As an example, the motors may be servomotors that are coupled with sensors for positioning feedback and coupled with controllers for precisely controlling the position, velocity, and/or acceleration of the motors. Each motor for the assemblies 26, 28 may include a dedicated module for controlling the motor or the motors may share a common module. In either case, and as seen in FIGS. 1-2, the controls for the motors may be controlled by a user device 34 (e.g., computer) that may be operated by a user (e.g., surgeon). Considering the complexity of the various movements associated with all the motors in the surgical table 10, the user device 34 may coordinate the motion of all of the motors into simplified, preprogrammed commands that are common to the needs in a surgical environment.

Figure 32:
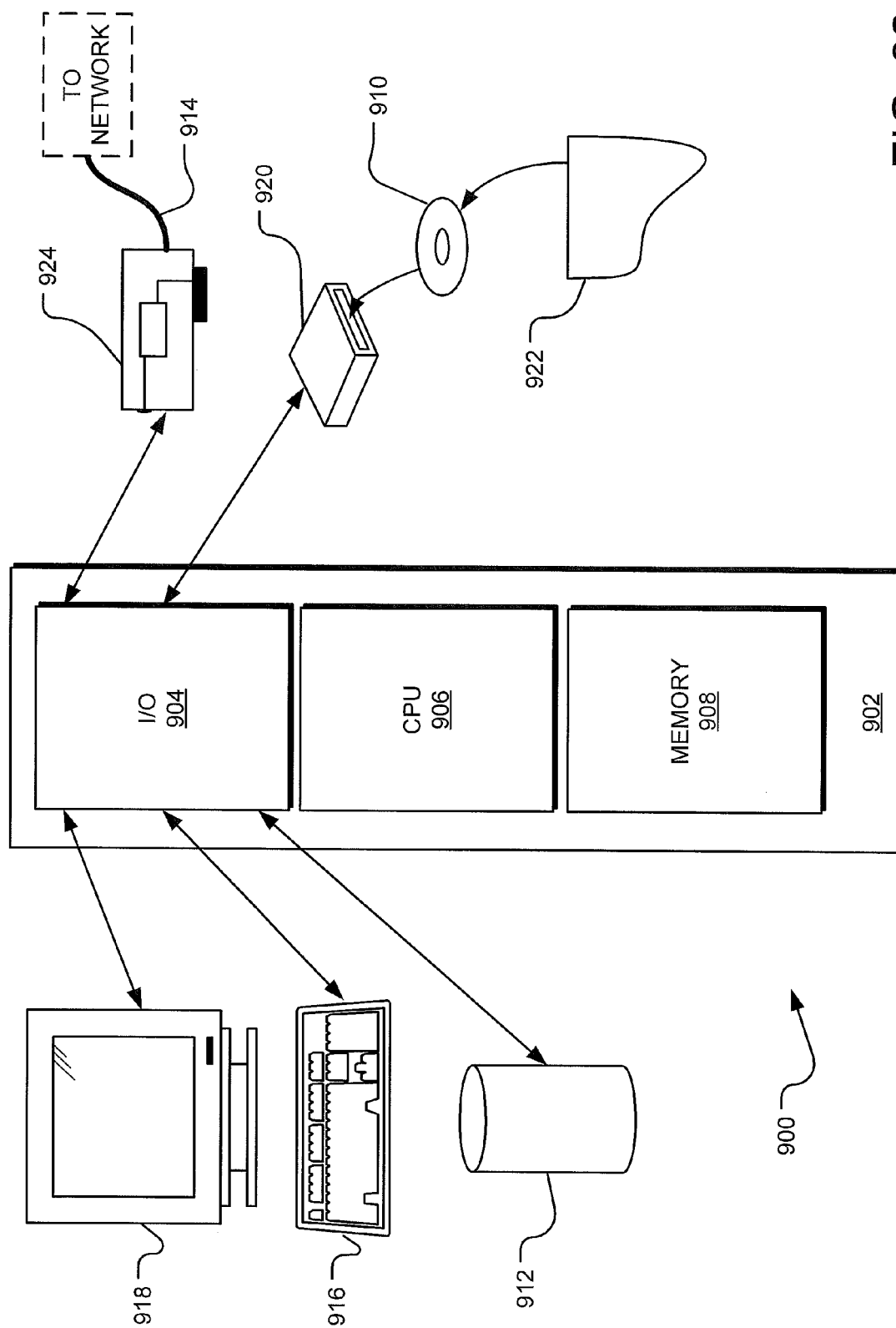
FIG. 32 depicts an example computer system for implementing the methods described herein.

Such coordinated movement, as described previously, may require the motors to be in communication with a computing system. Reference is now made to FIG. 32, which is an example computing system 900 having one or more computing units that may implement various systems and methods discussed herein is provided. The computing system 900 may be applicable to the user device 34, a server in communication with a network, or other computing devices. It will be appreciated that specific implementations of these devices may be of differing possible specific computing architectures not all of which are specifically discussed herein but will be understood by those of ordinary skill in the art.

The computer system 900 may be a general computing system is capable of executing a computer program product to perform a computer process. Data and program files may be input to the computer system 900, which reads the files and executes the programs therein. Some of the elements of a general purpose computer system 900 are shown in FIG. 32 wherein a processor 902 is shown having an input/output (I/O) section 904, a Central Processing Unit (CPU) 906, and a memory section 908. There may be one or more processors 902, such that the processor 902 of the computer system 900 comprises a single central-processing unit 906, or a plurality of processing units, commonly referred to as a parallel processing environment. The computer system 900 may be a conventional computer, a distributed computer, or any other type of computer, such as one or more external computers made available via a cloud computing architecture. The presently described technology is optionally implemented in software devices loaded in memory 908, stored on a configured DVD/CD-ROM 910 or storage unit 912, and/or communicated via a wired or wireless network link 914, thereby transforming the computer system 900 in FIG. 32 to a special purpose machine for implementing the described operations.

The I/O section 904 is connected to one or more user-interface devices (e.g., a keyboard 916 and a display unit 918), a disc storage unit 912, and a disc drive unit 920. In the case of a tablet, a smart phone device, or similar computing device, there may not be a physical keyboard but rather a touch screen with a computer generated touch screen keyboard. Generally, the disc drive unit 920 is a DVD/CD-ROM drive unit capable of reading the DVD/CD-ROM medium 910, which typically contains programs and data 922. Computer program products containing mechanisms to effectuate the systems and methods in accordance with the presently described technology may reside in the memory section 904, on a disc storage unit 912, on the DVD/CD-ROM medium 910 of the computer system 900, or on external storage devices made available via a cloud computing architecture with such computer program products, including one or more database management products, web server products, application server products, and/or other additional software components. Alternatively, a disc drive unit 920 may be replaced or supplemented by an optical drive unit, a flash drive unit, magnetic drive unit, or other storage medium drive unit. Similarly, the disc drive unit 920 may be replaced or supplemented with random access memory (RAM), magnetic memory, optical memory, and/or various other possible forms of semiconductor based memories.

The network adapter 924 is capable of connecting the computer system 900 to a network via the network link 914, through which the computer system can receive instructions and data. Examples of such systems include personal computers, Intel or PowerPC-based computing systems, AMD-based computing systems and other systems running a Windows-based, a UNIX-based, or other operating system. It should be understood that computing systems may also embody devices such as terminals, workstations, personal computers, mobile phones, tablets or slates, multimedia consoles, gaming consoles, set top boxes, etc.

When used in a LAN-networking environment, the computer system 900 is connected (by wired connection or wirelessly) to a local network through the network interface or adapter 924, which is one type of communications device. When used in a WAN-networking environment, the computer system 900 typically includes a modem, a network adapter, or any other type of communications device for establishing communications over the wide area network. In a networked environment, program modules depicted relative to the computer system 900 or portions thereof, may be stored in a remote memory storage device. It is appreciated that the network connections shown are examples of communications devices for and other means of establishing a communications link between the computers may be used.

In an example implementation, table articulation data, imaging data, patient data, a plurality of internal and external databases, source databases, and/or cached data on servers are stored as the memory 908 or other storage systems, such as the disk storage unit 912 or the DVD/CD-ROM medium 910, and/or other external storage devices made available and accessible via a network architecture. Table articulation software, imaging software, and other modules and services may be embodied by instructions stored on such storage systems and executed by the processor 902.

Some or all of the operations described herein may be performed by the processor 902. Further, local computing systems, remote data sources and/or services, and other associated logic represent firmware, hardware, and/or software configured to control operations of the surgical table 10, the user device 34, and/or other computing units or components in communication with the surgical table 10 and/or the user device 34. Such services may be implemented using a general purpose computer and specialized software (such as a server executing service software), a special purpose computing system and specialized software (such as a mobile device or network appliance executing service software), or other computing configurations. In addition, one or more functionalities disclosed herein may be generated by the processor 902 and a user may interact with a Graphical User Interface (GUI) using one or more user-interface devices (e.g., the keyboard 916, the display unit 918, and the user device 34). The system set forth in FIG. 32 is but one possible example of a computer system that may employ or be configured in accordance with aspects of the present disclosure.

Although various representative embodiments of this invention have been described above with a certain degree of particularity, those skilled in the art could make numerous alterations to the disclosed embodiments without departing from the spirit or scope of the inventive subject matter set forth in the specification. All directional references (e.g., distal, proximal, front, back, side, top, bottom, fore, aft) are only used for identification purposes to aid the reader's understanding of the embodiments of the present invention, and do not create limitations, particularly as to the position, orientation, or use of the invention unless specifically set forth in the claims. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other.

In methodologies directly or indirectly set forth herein, various steps and operations are described in one possible order of operation, but those skilled in the art will recognize that steps and operations may be rearranged, replaced, or eliminated without necessarily departing from the spirit and scope of the present invention. It is intended that all matter contained in the above description or shown in the accompanying drawings shall be interpreted as illustrative only and not limiting. Changes in detail or structure may be made without departing from the spirit of the invention as defined in the appended claims.

What is claimed is:

1. A surgical table comprising:
a patient support structure and a base assembly comprising a first and a second support column supporting respective ends of the patient support structure,
the patient support structure comprising a head end section and a foot end section, the head end section coupled at an outer end thereof to the first support column, the foot end section coupled at an outer end thereof to the second support column, the head and foot end sections each comprising a pair of inner ends that are pivotally and slidingly coupled together at an inward articulation, each of the inner ends of the head end section comprise a slot at the inward articulation, each of the inner ends of the foot end section are coupled with the respective slot at the inward articulation via a hinge pin that engages the slot, the hinge pin being configured to pivot and slide within the slot, the head end section and foot end section articulating about a hinge axis extending through the hinge pin,
wherein the hinge pin is positionally located in between a head end portion and a foot end portion of the slot when the head and foot end sections are in a neutral position, and
wherein the hinge pin is configured to move towards a foot end portion of the slot when the patient support structure moves from the neutral position to an extended position.

2. The surgical table of claim 1, wherein the neutral position is when the head end section and the foot end section are substantially parallel.

3. The surgical table of claim 1, wherein the extended position is when a topside angle between the head and foot end sections is less than one hundred eighty degrees.

4. The surgical table of claim 1, wherein the hinge pin moves towards the head end portion of the slot when the patient support structure moves from the neutral position to a flexed position.

5. The surgical table of claim 4, wherein the flexed position is when a topside angle between the head and foot end section is greater than one hundred eighty degrees.

6. The surgical table of claim 1, wherein the slot is a substantially stadium-shaped opening.

7. The surgical table of claim 1, wherein the head end portion of the slot is nearer the outer end of the head end section than the foot end portion of the slot.

8. The surgical table of claim 1, wherein the foot end portion of the slot is nearer the outer end of the foot end section than the head end portion of the slot.

9. The surgical table of claim 1, wherein the slot is angled downward from the head end section by about twenty degrees.

10. The surgical table of claim 1, wherein the hinge pin is positionally located at or near a foot end of the slot when the head and foot end sections define a topside angle that is less than one hundred eighty degrees, the hinge pin is positionally located at or near the head end portion of the slot when the topside angle is greater than one hundred eighty degrees.

11. The patient support of claim 1, wherein the hinge pin is fixedly coupled to the inner ends of the foot end section.

12. The patient support of claim 1, wherein the patient support structure including the hinge pin comprises a radiolucent material.

13. A surgical table comprising:
a base assembly comprising a pair of spaced apart end support columns; and a patient support structure comprising a head end section and a foot end section, the head end section comprising a pair of head end members coupled on outer ends with one of the pair of end support columns, the foot end section comprising a pair of foot end members coupled on outer ends with another of the pair of end support columns, each of the head end members comprising an inner end with a slot formed therein, each of the foot end members coupled with a respective inner end of the head end member at the slot by a hinge pin configured to pivot and translate within the slot when the head and foot end sections articulate relative to each other, wherein a distance between the hinge pin and the outer ends of the head end members is configured to increase or decrease when the head end section and the foot end section articulate relative to each other about a hinge axis extending through the hinge pin.

14. The surgical table of claim 13, wherein the slot comprises an opening including a head end portion at one end of the slot and a foot end portion at another end of the slot, the head end portion nearer the outer end of the head end member.

15. The surgical table of claim 14, wherein the hinge pin is positioned near a mid-point between the head end portion and the foot end portion of the slot when the head end section and the foot end section are in a neutral position.

16. The surgical table of claim 15, wherein the head end section and the foot end section are substantially parallel in the neutral position.

17. The surgical table of claim 13, wherein the hinge pin is positioned at or near the head end portion when the head end section and the foot end section are in a flexed position.

18. The surgical table of claim 17, wherein the head end section and the foot end section define a topside angle of more than one hundred eighty degrees in the flexed position.

19. The surgical table of claim 13, wherein the hinge pin is positioned at or near the foot end portion when the head end section and the foot end section are in an extended position.

20. The surgical table of claim 19, wherein the head end section and the foot end section define a topside angle of less than one hundred eighty degrees in the extended position.

21. The surgical table of claim 13, wherein another distance between the hinge pin and the outer ends of the foot end members is configured to remain substantially constant when the head end section and the foot end section articulate relative to each other about the hinge pin.

22. The surgical table of claim 13, wherein the slot extends along a first longitudinal axis that is angled downward about twenty degrees from a second longitudinal axis of the head end members.

23. A patient support structure coupled to a base of a surgical table, the patient support structure comprising:
 a head end section and a foot end section that are pivotally and slidingly coupled together at an articulation, the head end section comprising a slot at the articulation, the foot end section being coupled with the slot at the articulation via a hinge pin that engages the slot, the hinge pin being configured to pivot and slide within the slot, the head end section and foot end section articulating about a hinge axis extending through the hinge pin,
 wherein the hinge pin is positionally located in between a head end portion and a foot end portion of the slot when the head and foot end sections are in a neutral position, and
 wherein the hinge pin is configured to move towards a foot end portion of the slot when the patient support structure moves from the neutral position to an extended position.

24. The patient support of claim 23, wherein the head end section comprises a pair of spaced apart head end members, and the foot end section comprises a pair of spaced apart foot end members.

25. The patient support of claim 24, wherein each of head end members comprises the slot at the articulation, such that each head end member is pivotally and slidingly coupled with an inner end of a corresponding foot end member at the articulation via a respective hinge pin.

26. The patient support of claim 23, wherein the neutral position is when the head end section and the foot end section are substantially parallel.

27. The patient support of claim 23, wherein the extended position is when a topside angle between the head and foot end sections is less than one hundred eighty degrees.

28. The patient support of claim 23, wherein the hinge pin moves towards the head end portion of the slot when the patient support structure moves from the neutral position to a flexed position.

29. The patient support of claim 26, wherein the flexed position is when a topside angle between the head and foot end section is greater than one hundred eighty degrees.

30. The patient support of claim 23, wherein the slot is a substantially stadium-shaped opening.

31. The patient support of claim 23, wherein the head end portion of the slot is nearer the outer end of the head end section than the foot end portion of the slot.

32. The patient support of claim 23, wherein the foot end portion of the slot is nearer the outer end of the foot end section than the head end portion of the slot.

33. The patient support of claim 23, wherein the slot is angled downward from the head end section by about twenty degrees.

34. The patient support of claim 23, wherein the hinge pin is positionally located at or near a foot end of the slot when the head and foot end sections define a topside angle that is less than one hundred eighty degrees, the hinge pin is positionally located at or near the head end portion of the slot when the topside angle is greater than one hundred eighty degrees.

35. A patient support structure for supporting a patient on a surgical table comprising a base, the patient support structure comprising:
 a head end section;
 a foot end section coupled to the base of the surgical table;
 a torso assembly removably coupled to the head end section;
 a hip pad attached to the foot end section;
 a sliding hinge that pivotally and slidably couples the head and foot end sections, wherein each of head end members comprises a slot at the articulation such that each head end member is pivotally and slidingly coupled with an inner end of a corresponding foot end member at the articulation via a hinge pin that engages the respective slot, the hinge pin being configured to pivot and slide with the respective slot, the head end section and foot end section articulating about a hinge axis extending through the hinge pin;
 wherein the sliding hinge allows for adjustment of a longitudinal distance between the torso assembly and the hip pad to compensate for movement of the patient supported on the torso assembly and the hip pad when the head and foot end sections transition from a neutral position to an extended position or a flexed position.

36. The patient support of claim 35, wherein the neutral position is when the head end section and the foot end section are substantially parallel.

37. The patient support of claim 35, wherein the extended position is when a topside angle between the head and foot end sections is less than one hundred eighty degrees.

38. The patient support of claim 35, wherein the hip pad moves towards the torso assembly when the head and foot end sections transition from the neutral position to the flexed position.

39. The patient support of claim 35, wherein the flexed position is when a topside angle between the head and foot end section is greater than one hundred eighty degrees.

40. The patient support of claim 35, wherein the hip pad moves away from the torso assembly when the head and foot end sections transition from the neutral position to the extended position.

41. The patient support of claim 35, wherein the extended position is when a topside angle between the head and foot end section is smaller than one hundred eighty degrees.

42. The patient support of claim 35, wherein the head end section comprises a pair of spaced apart head end members, and the foot end section comprises a pair of spaced apart foot end members.

\* \* \* \* \*